(12) United States Patent
Levitt et al.

(10) Patent No.: US 7,166,462 B2
(45) Date of Patent: Jan. 23, 2007

(54) METHODS AND SYSTEMS FOR FACILITATING THE DIAGNOSIS AND TREATMENT OF SCHIZOPHRENIA

(75) Inventors: Pat Ressler Levitt, Pittsburgh, PA (US); Venkata Chowdari Kodavali, Pittsburgh, PA (US); Vishwajit Laxmikant Nimgaonkar, Pittsburgh, PA (US); Karolyn Mirnics, Pittsburgh, PA (US)

(73) Assignee: Vanderbult University, Nashville, TN (US)

( * ) Notice: Subject to any disclaimer, the term of this patent is extended or adjusted under 35 U.S.C. 154(b) by 0 days.

(21) Appl. No.: 09/939,209

(22) Filed: Aug. 24, 2001

(65) Prior Publication Data

US 2003/0113721 A1 Jun. 19, 2003

Related U.S. Application Data

(60) Provisional application No. 60/228,021, filed on Aug. 24, 2000.

(51) Int. Cl.
*C12N 15/85* (2006.01)
*C07H 21/04* (2006.01)
*C12N 15/11* (2006.01)

(52) U.S. Cl. .................. 435/325; 536/23.1; 536/24.31

(58) Field of Classification Search ............... 536/23.1, 536/24.31, 24.32, 24.5; 435/320.1, 325
See application file for complete search history.

(56) References Cited

U.S. PATENT DOCUMENTS 6,210,879 B1 4/2001 Meloni et al.

OTHER PUBLICATIONS

Adams et al. Human STS sequence. G32908. Sep. 24, 1999.*
*Principles of Neural Science*, 3rd ed., 1991, Kandel, Schwartz, and Jessel (Eds.), Connecticut: Appleton & Lange, pp. 853-868; Chapter 55.
Brzustowica et al. (2000) *Science* 288: 678-82.
Druey et al. (1996) *Nature* 379: 742-746.
Nomoto et al. (1997) *Biochem. Biophys. Res. Commun.* 241(2): 281-287.
Glantz and Lewis (2000) *Arch. Gen. Psych.* 54: 943-952.
Campbell et al. (1999) *Exp. Neurol.* 160: 268-278.
Nurnberger et al. (1994) *Arch. Gen. Psych.* 51: 849-59; 863-4.
Cloninger et al. (1998) *Am. J. Med. Gen.* 81: 275-81.
Kruglyak et al. (2001) *Nature Gen.* 27: 234-236.
Mirnics et al. (2001) *Mol. Psych.* 6: 293-301.
Orita et al. (1989) *PNAS* 86: 2766-70.
Faraone et al. (1998) *Am. J. Med. Gen.* 81: 290-5.
O'Connell et al. (1998) *Am. J. Hum. Gen.* 63: 259-266.
Kruglyak et al. (1996) *Am. J. Hum. Gen.* 58: 1347-63.
Spielman et al. (1994) *Am. J. Hum. Gen.* 54: 559-60.
Clayton et al. (1999a) *Am. J. Hum. Gen.* 65: 1161-1169.
Clayton et al. (1999b) *Am. J. Hum. Gen.* 65: 1170-1177.
Palmiter and Brinster (1986) *Ann. Rev. Genet.* 20: 465-499.
Gordon (1989) *Intl. Rev. Cytol.* 115: 171-299.
Nebert et al. (2000) *Ann. N.Y. Acad. Sci.* 919: 148-170.
Taylor et al. (2001) Poster presentation from the Society for Neuroscience national meeting.
Libin, B. JIA et al.: "Human bone narrow stromal cells Homo sapiens cDNA clone" retrieved from EMBL. accession No. AI754847 Database accession No. AI754847; DATABASE EBI Online! EMBL: Jun. 29, 1999.
Strausberg, R.: "H. sapiens cDNA clone" retrieved from EMBL accession No. AA595701 Database accession No. AA595701; DATABASE EBI Online! EMBL Sep. 24, 1997.
Abola, A. P. et al.: "Homo sapiens chromosome 1 clone RP11-288018" retrieved from EMBL.: accession No. AC031977 Database accession No. AC031977; DATABASE EBI Online! EMBL: Apr. 5, 2000.
Druey, Kirk M et al.: "Inhibition of regulator of G protein signaling function by two mutant RGS4 proteins." Proceedings of the National Academy of Sciences of the United States, vol. 94, No. 24, Nov. 25, 1997, pp. 12851-12856.
Srinivasa, S P et al.: "Plasma membrane localization is required for RGS4 function in *Saccharomyces cerevisiae*," Proceedings of the National Academy of Sciences of the United States of America, United States May 12, 1998, vol. 95, No. 10, pp. 5584-5589.
Pulver, A E: "Search for Schizophrenia susceptibility genes" Biological Psychiatry, Elsevier Science, New York, NY, US, vol. 47, Feb. 1, 2000, pp. 221-230.
De Vries, L et al.: "The regulator of G protein signaling family," Annual Review of Pharmacology and Toxicology, United States 2000, vol. 40, 2000, pp. 235-271.
Hepler, Jr: "Emerging roles for RGS proteins in cell signalling" Trends in Pharmacological Sciences, Elsevier Trends Journal, Cambridge. GB, vol. 20, No. 9, Sep. 1, 1999, pp. 376-382.
Ni Yan G et al.: "Region-specific regulation of RGS4 (regulator of G-protein-signaling protein type 4) in brain by stress and glucocorticoids: In vivo and in vitro studies," Journal Of Neuroscience vol. 19, No. 10, May 15, 1999, pp. 3674-3680.

* cited by examiner

*Primary Examiner*—Celine Qian
(74) *Attorney, Agent, or Firm*—Reed Smith LLP

(57) ABSTRACT

A method of diagnosing, assessing susceptibility, and/or treating schizophrenia involving the observation of regulator of G-protein signaling 4 (RGS4) levels in a subject. Embodiments of the present invention include increasing RGS4 expression levels in the cortex, either by chemical means or by genetic complementation (e.g. gene therapy).

5 Claims, 8 Drawing Sheets

METHODS AND SYSTEMS FOR FACILITATING THE DIAGNOSIS AND TREATMENT OF SCHIZOPHRENIA

This application claims the benefit under 35 U.S.C. §119(e) of U.S. Provisional Application No. 60/228,021, filed Aug. 24, 2000.

This invention was made with United States Government support in the form of Grant Nos. MH45156, MH01489, MH56242, MH53459, and MH45156 from the National Institute of Mental Health. The United States Government may have certain rights in the invention.

FIELD OF THE INVENTION

The present invention relates generally to the field of neurological and physiological dysfunctions associated with schizophrenia. The invention further relates to the identification, isolation, and cloning of genes which, when mutated or varied, are associated with schizophrenia. The present invention also relates to methods for diagnosing and detecting carriers of the genes and to diagnosis of schizophrenia. The present invention further relates to the construction of animal models of schizophrenia.

BACKGROUND OF THE INVENTION

Schizophrenia is a serious brain disorder that affects approximately 1% of the human population. The cause of this complex and devastating disease remains elusive, although genetic, nutritional, environmental, and developmental factors have been considered. A combination of clinical, neuroimaging, and postmortem studies have implicated the dorsal prefrontal cortex (PFC) as a prominent site of dysfunction in schizophrenia.

Schizophrenia is typically characterized as a disorder of thinking and cognition, as contrasted to other disorders of mental faculties, such as mood, social behavior, and those affecting learning, memory, and intelligence. Schizophrenia is characterized by psychotic episodes during which an individual may lose the ability to test reality or may have hallucinations, delusions, incoherent thinking, and even disordered memory. There are varying forms of schizophrenia differing in severity, from a schizotypal disorder to a catatonic state. A review of schizophrenia can be found in *Principles of Neural Science*, $3^{rd}$ ed., 1991, Kandel, Schwartz, and Jessel (Eds.), Connecticut: Appleton & Lange, pp. 853–868; of which Chapter 55 is incorporated herein by reference.

Diseases of organ systems, such as those of the heart, lung, and kidney, are usually confirmed by tissue pathology. A demonstrable pathology includes identifying and defining a structural abnormality in the organ, along with an associated alteration in organ function. This type of diagnosis is also utilized in certain neurological diseases. However, there are few psychiatric disorders in which clinical manifestations and symptoms can be correlated with a demonstrable pathology. The majority of mental illnesses are evaluated by observing changes in key behaviors such as thinking, mood, or social behavior. These alterations are difficult to ascertain and nearly impossible to quantify. However, progress is being made in diagnosing mental illness and in determining the neuropathology of mental illnesses.

The Diagnostic and Statistical Manual of Mental Disorders, Third Edition (DSM-III-R) and the updated DSM-IV, published by the American Psychiatric Association, represent the progress made in providing a basis for objective and rigorous descriptive criteria for categories of psychiatric disorders. While the DSM-III-R is very thorough and detailed, it is also quite lengthy. Thus, the process of reviewing the categories and applying them to data from a patient is also very time-consuming and arduous. In addition, there is no mechanism by which a patient can be diagnosed either as having or being susceptible to schizophrenia prior to the expression of symptoms. Thus, there is a longstanding need for an easy and definitive method for diagnosing schizophrenia. A diagnostic tool that can be applied prior to the expression of symptoms would also have great utility, providing a basis for the development of therapeutic interventions.

There is strong evidence for a genetic linkage of schizophrenia. Historically, there have been a number of studies on monozygotic twins of schizophrenics that indicated that 30–50% of the twins also had schizophrenia. The fact that this number is not 100% indicates that there are other factors involved in this disease process that may protect some of these individuals from the disease. It is apparent from a number of studies that the patterns of inheritance in most forms of schizophrenia are more complex than the classical dominant or recessive Mendelian inheritance. Recently, locus 1q21-22, a chromosome region containing several hundred genes, has been strongly linked to schizophrenia as shown by Brzustowicz et al., *Science* 288, 678–82, 2000, which is hereby incorporated by reference.

Until the 1950's there were no specific, effective treatments for schizophrenia. Antipsychotic drugs were identified in the 1950's, and these drugs were found to produce a dramatic improvement in the psychotic phase of the illness. Reserpine was the first of these drugs to be used and was followed by typical antipsychotic drugs including phenothiazines, the butyrophenones, and the thioxanthenes. A new group of therapeutic drugs, typified by clozapine, has been developed and were referred to as "a typical" antipsychotics. Haloperidol has been employed extensively in the treatment of schizophrenia and is one of the currently preferred options for treatment. When these drugs are taken over the course of at least several weeks, they mitigate or eliminate delusions, hallucinations, and some types of disordered thinking. Maintenance of a patient on these drugs reduces the rate of relapse. Since there is no way of determining if an individual is susceptible to schizophrenia, it is currently unknown if these antipsychotic compounds are useful in the prophylactic treatment of schizophrenia.

Signal transduction is the general process by which cells respond to extracellular signals (e.g. neurotransmitters) through a cascade of biochemical reactions. The first step in this process is the binding of a signaling molecule to a cell membrane receptor that typically leads to the inhibition or activation of an intracellular enzyme. This type of process regulates many cell functions including cell proliferation, differentiation, and gene transcription.

One important mechanism by which signal transduction occurs is through G-proteins. Receptors on the cell surface are coupled intracellularly to a G-protein that becomes activated, when the receptor is occupied by an agonist, by binding to the molecule GTP. Activated G-proteins may influence a large number of cellular processes including voltage-activated calcium channels, adenylate cyclase, and phospholipase C. The G-protein itself is a critical regulator of the pathway by virtue of the fact that GTPase activity in the G-protein eventually hydrolyzes the bound GTP to GDP, restoring the protein to its inactive state. Thus, the G-protein contains a built-in deactivation mechanism for the signaling process.

Recently, an additional regulatory mechanism has been discovered for G-protein signaling that involves a family of mammalian gene products termed regulators of G-protein signaling, or RGS (Druey et al., 1996, Nature 379: 742–746 which is hereby incorporated by reference). RGS molecules play a crucial modulatory role in the G-protein signaling pathway. RGS proteins bind to the GTP-bound Gα subunits with a variable Gα specificity as a substrate. RGS molecules shorten the GTP binding of the activated Gα subunits by acting as GTPase activating proteins (GAPs), accelerating GTP hydrolysis by up to one hundred fold. By the virtue of this GAP action and by making available the GDP-bound Gα to re-attach to βγ dimers, RGS proteins shorten the duration of the intracellular signaling. RGS proteins are expressed in nearly every cell; however, they show a tissue-specific expression across the body and cell type-specific expression in the brain. For example, RGS4 is strongly expressed in the central nervous system, moderately expressed in the heart, and slightly expressed in skeletal muscle (Nomoto et al., 1997, Biochem. Biophys. Res. Commun. 241(2):281–287 which is herein incorporated by reference).

Several members of the G-protein signaling pathways, most located downstream of RGS4 modulation, have been implicated in schizophrenia. Gil, Gq and Golf messenger RNA (mRNA) and protein levels all have been reported to be altered in various brain regions of the schizophrenic subjects. Furthermore, changes in expression of adenylate cyclase, phospholipase C, and protein kinases, as well as DARPP (dopamine- and cAMP-regulated phosphoprotein) phosphorylation changes are expected to be influenced by RGS regulation of Gα signaling. In addition, RGS modulation changes are expected to have significant effects on the signal transduction effected by neurotransmitters including dopamine, serotonin, GABA, glutamate, and norepinephrine.

An additional genetic marker of schizophrenia has been identified by Meloni et al. (U.S. Pat. No. 6,210,879). These investigators found that an allele of the microsatellite HUNTH01 in the tyrosine hydroxylase gene correlated with the expression of schizophrenia. However, the allele only appears to be present in sporadic schizophrenias.

There has been a long-standing need for a definitive and easy method for diagnosing schizophrenia as well as for an effective treatment with minimal side effects. Further, a need has been recognized in connection with being able to detect schizophrenia prior to the expression of noticeable symptoms.

A need has been recognized in connection with overcoming the various limitations to the current implementation of a method for diagnosing and assessing the susceptibility to schizophrenia are addressed through the use of the current invention.

SUMMARY OF THE INVENTION

In accordance with at least one embodiment of the present invention, there is provided a system and method for diagnosing and determining the susceptibility to schizophrenia.

In summary, one aspect of the present invention provides an isolated and substantially purified DNA sequence corresponding to SEQ ID NOS: 3, 4, 5, 6, 7, 8, and contiguous portions thereof.

Another aspect of the present invention is a polynucleotide sequence that is complementary to a sequence selected from the group consisting of SEQ ID NO: 3, SEQ ID NO: 4, SEQ ID NO: 5, SEQ ID NO: 6, SEQ ID NO: 7, SEQ ID NO: 8, and contiguous protions thereof.

A further aspect of the present invention is an expression system comprising a DNA sequence that corresponds to SEQ ID NO:3.

A yet further aspect of the present invention is a method for diagnosing schizophrenia in a human comprising obtaining a DNA sample comprising a RGS4 gene from a patient and detecting a variation in the RGS4 gene indicating schizophrenia.

A still further aspect of the present invention is a method for determining the susecptiblity to schizophrenia comprising obtaining from a patient a DNA sample comprising a RGS4 gene and detecting a variation in said RGS4 gene indicating susceptibility to schizophrenia.

An additional aspect of the present invention is a method for daignosing schizophrenia comprising obtaining from a patient to be tested for schizophrenia a sample of tissue, measuring RGS4 mRNA levels in said sample, and determing if there is a reduced level of RGS4 mRNA in the sample.

A still additional aspect of the present invention is a method of determing susceptibility to schizophrenia comprising obtaining from a patient to be tested for susceptibility to schizophrenia a sample of tissue, measuring RGS4 mRNA levels in said sample, and determing if there is a reduced level of RGS4 mRNA in the sample.

A yet further aspect of the present invention is A method of determining susceptibility to schizophrenia comprising obtaining from a patient to be tested for susceptibility to schizophrenia a sample of tissue, measuring RGS4 protein levels in said sample, and determining if there is a reduced level of RGS4 protein in the sample.

Yet another aspect of the present invention is A method of treating schizophrenia, said method comprising measuring RGS4 protein or mRNA levels in a patient, and altering said RGS4 protein levels to provide the patient with an improved psychiatric function.

Another aspect of the present invention is a kit for diagnosising schizophrenia in a patient, said kit comprising antibodies to RGS4, and a detector for ascertaining whether said antibodies bind to RGS4 in a sample.

Another aspect of the present invention is a kit for diagnosising schizophrenia in a patient, said kit comprising a detect of RGS4 transcript levels in a patient, and a standard to ascertain altered levels of RGS4 transcript in the patient.

A still further aspect of the present invention is the DNA sequence of SEQ ID NO: 3 containing variations as described in the text below.

A yet further aspect of the present invention is a transgenic mouse whose genome comprises a disruption of the endogenous RGS4 gene, wherein said disruption comprises the insertion of a transgene, and wherein said disruption results in said transgenic mouse not exhibiting normal expression of RGS4 protein.

A still additional aspect of the present invention is a transgenic mouse wherein a transgene comprises a nucleotide sequence that encodes a selectable marker.

These and other embodiments and advantages of the present invention will be better understood with reference to the following figures and detailed description.

BRIEF DESCRIPTION OF THE DRAWINGS

The present invention and its presently preferred embodiments will be better understood by reference to the detailed disclosure hereinbelow and to the accompanying drawings, wherein.

DESCRIPTION OF THE PREFERRED EMBODIMENTS

Figure 1A:
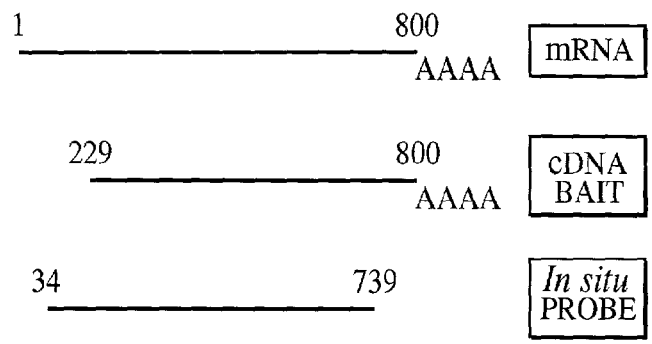
FIG. 1A displays the design of microarray immobilized probes and in situ probes for RGS4, wherein numbers on the RGS4 nucleic acid fragments denote nucleotide position in relationship to the RGS4 mRNA, as currently in the NCBI database.

The present invention focuses on the genetic underpinnings of schizophrenia. In the first phase of the research, cDNA microarrays were used to investigate potential alterations in transcript expression in six pairs of schizophrenic subjects. RGS4 was determined to be the most significantly and consistently changed transcript. In situ hybridization was also used to verify the microarray findings and to examine the regional and disease-related specificity of this change. Out of the several hundred genes on locus 1q21-22, the present studies indicate that RGS4 is a strong candidate for a major susceptibility gene on this locus. Genetic association and linkage studies were conducted using two samples independently in Pittsburgh and by the NIMH Collaborative Genetics Initiative. Using the Transmission Disequilibrium Test (TDT), significant transmission distortion was observed in both samples, albeit with different haplotypes. In support of the TDT results, increased sharing of alleles, identical by descent was observed for polymorphisms in this region among affected siblings of the NIMH cases, though associations were not observed when the cases were compared to a limited number of population-based controls. These analyses are consistent with the possibility that inheritable polymorphisms in the flanking untranslated regions (UTR) of the RGS4 gene confer susceptibility to schizophrenia.

Expression Studies

Two groups of human subjects, consisting of six and five pairs of schizophrenic and control subjects, were used in the present studies. Subject pairs were completely matched for sex (18 males and 4 females). The mean (±SD) difference within pairs was 4.6±3.5 years for age and 4.4±2.7 hours for post mortem interval (PMI). The entire group of schizophrenic and control subjects did not differ in mean (±SD) age at time of death (46.5±10.7 and 45.1±11.5 years, respectively), PMI (19.4±7.1 and 17.7±5.0 hours, respectively), brain pH (6.85±0.29 and 6.81±0.15, respectively), or tissue storage time at −80° C. (45.4±12.3 and 37.7±13.1 months, respectively) when the studies initiated. Nine of the schizophrenic subjects were receiving antipsychotic medications at the time of death, five had a history of alcohol abuse or dependence, and one died by suicide. Also studied were 10 subjects with major depressive disorder (MDD), each of whom were matched to one normal control subject. The MDD subject pairs were also completed matched for sex (18 males and 2 females). The mean (S.D.) difference within pairs was 1.2±1.4 years for age and 2.5±2.1 hours for PMI. The depressive and control subjects did not differ in mean (±S.D.) age at time of death (52.7±13.1 and 52.1±13.1 years, respectively), PMI (14.9±5.3 and 15.7±5.5 hours, respectively), brain pH (6.81±0.17 and 6.72±0.30), or tissue storage time at −80° C. (39.0±17.4 and 39.9±13.2 months, respectively). Two of the depressed subjects had a history of alcohol dependence, and six died by suicide. Two of the control subjects had also been matched to subjects with schizophrenia (685c, 604c). Consensus DSM-IIIR diagnoses were made for all subjects using data from clinical records, toxicology studies, and structured interviews with surviving relatives.

RCS4 Transcript Analysis

Figure 6:
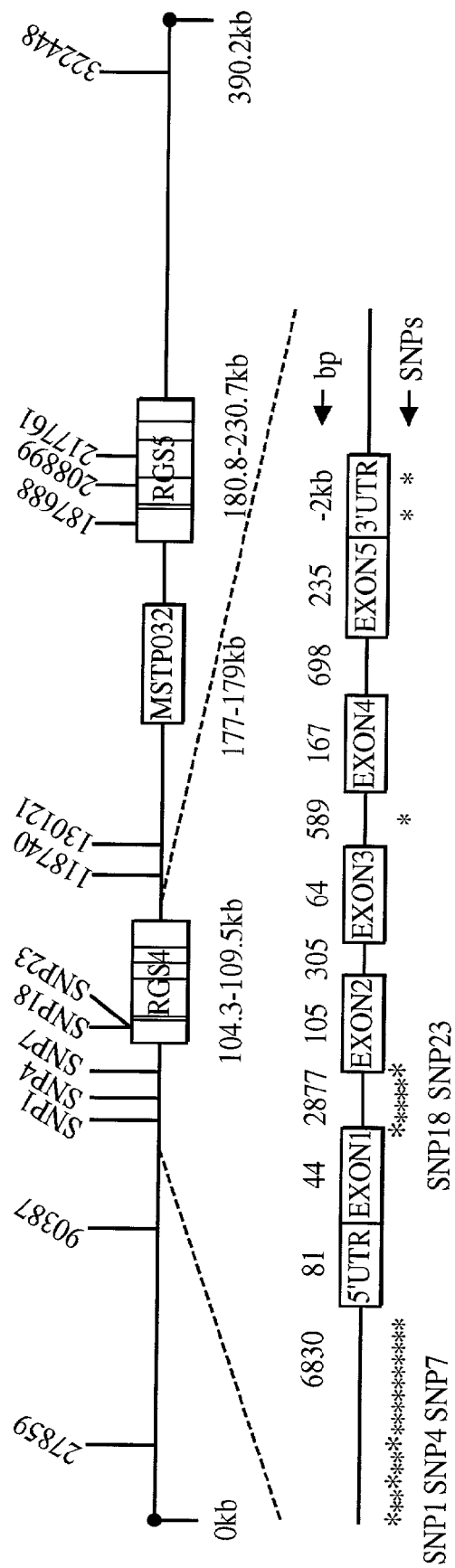
FIG. 6 displays the genomic organization that is derived from available sequences for clone NT_022030, as well as the sequence analyses presented here; five exons were identified from the coding sequence for RGS4 (approximately 8.5 kb); the critical RGS domain is encoded by exons 3 to 5; the SNPs that were analyzed are listed in the top panel; * (a small star) indicates SNPs identified by re-sequencing the RGS4 gene and * (a large star) indicates SNPs used for association analysis.

A Human Multiple Tissue Northern Blot (Clontech) and a $^{32}$P-labeled cDNA probe were used to confirm the size of the RGS4 transcript reported previously (Druey, et al., 1996). However, our results reported the presence of single dark bands of ~3 kB in lanes from multiple brain regions (whole cerebral cortex, frontal pole, occipital pole, temporal lobe), with much fainter or absent bands observed in lanes from other brain regions (cerebellum, medulla, spinal cord, putamen). Because the UniGene entry for the RGS4 cDNA (U27768) contained only the truncated transcript (800 bp), we designed custom PCR primers based on the BAC clone sequence containing the RGS4 gene (NT_022030) to rapidly obtain the full-lenght RGS4 transcript sequence. For this analysis, mRNA from a control human brain was purified, DNased, and re-purified prior to first strand cDNA synthesis using Superscript II (Gibco) with an oligo dT primer. The resulting cDNA-mRNA mixture was diluted and used in a standard PCR reaction using AmpliTaq Gold (see above). All reaction products yielded single bright bands on 2% agarose/ethidium bromide-stained gels, and were subsequently purified and sequenced. Alignment of these sequences produced >99% identity matches with the BAC clone sequence containing RGS4. The 3' UTR for RGS4 obtained in this manner also aligned >99% with a cDNA entry (AL137433.1) that contains both a poly A signal and a poly A attachment site, confirming that the human RGS4 transcript is 2949 bp without the poly A tail and includes a cDNA entry not previously associated with the human transcript in the NCBI database (see below; FIG. 6).

Microarray Experiments

Fresh-frozen human tissue was obtained from the University of Pittsburgh's Center for the Neuroscience of Mental Disorders Brain Bank. Area 9 from the right hemisphere was identified and isolated and sectioned into tubes at −24° C. as described previously by Glantz, L. A. and Lewis, D. A. in Arch Gen Psychiatry 54: 943–952, 2000, which is herein incorporated by reference. Total RNA and mRNA were isolated according to manufacturer's instructions using Promega (Madison, Wis.) kit #Z5110, RNAgents® Total RNA Isolation System and Qiagen (Valencia, Calif.) kit #70022, Oligotex mRNA Kits, respectively. The volume was adjusted using Microcon columns YM-30 #42409 to 50 ng/µl. The quality and purity of the mRNA used in the reverse transcription labeling reactions was evaluated by size distribution on a 1% non-denaturing agarose gel (>50% of mRNA smear over 1 kb; integrity of rRNA bands) and optical density (OD) measurements (260/280>1.80), respectively.

Sample Labeling, Microarrays, Hybridization, and Data Analysis

Labeling was performed at Incyte Genomics, Inc. (Fremont, Calif.). Two hundred nanograms of mRNA was reverse transcribed using cy3- or cy5-labeled fluorescent primers; appropriate matched control and schizophrenic sample pairs were combined, and hybridized onto the same UniGEM-V cDNA microarray. Each UniGEM-V array contained over 7,000 unique and sequence-verified cDNA elements mapped to 6,794 UniGene Homo sapiens annotated clusters found at the NIH website. Hybridization and washing was performed using proprietary Incyte protocols. If a gene or expressed sequence tag (EST) was differentially expressed, the cDNA feature on the array bound more of the labeled probe from one sample than the other, producing either a greater cy3 or cy5 signal intensity. The microarrays were scanned under cy3-cy5 dual fluorescence, and the resulting images were analyzed for signal intensity. If the cy3 vs. cy5 signal intensity was within three fold, and the microarray detected spiked-in control standard less abundant than 1 copy in 50,000, the raw data were exported to a local SQL server database. On the server, the data were further analyzed using GemTools (Incyte's proprietary software) and MS-Excel 2000. Note that the operators performing the labeling, hybridization, scanning, and signal analysis were blind to the specific category to which each sample belonged.

A gene was considered to be expressed if the DNA sample was successfully amplified by PCR, produced signal from at least 40% of the spot surface, and had a signal/background ratio over 5-fold for either the cy3 or cy5 probe. Based on Incyte's control hybridization studies and control experiments, array data reliability and reproducibility cutoffs were established as follows:

1. Genes were comparably expressed between the control and experimental samples if the cy3/cy5 ratio or cy5/cy3 ratio was <1.6.
2. Gene expression was changed between the two samples at the 95% confidence level (95% CL) if the cy3/cy5 or cy5/cy3 signal was 1.6–1.89.
3. Gene expression was changed between the two samples at the 99% confidence level (99% CL) if the cy3/cy5 or cy5/cy3 signal was >1.9. In the control experiments, <0.5% of the observations fell into this category.

Gene Group Analysis

Of the genes represented on the array, a G-protein group was created for data analysis, and included transcripts on the microarray for G-protein-coupled receptors (GPCR), heterotrimeric G-protein subunits, Ras proteins, regulator of G-protein signaling (RGS) molecules, and G-protein-dependent inward rectifying potassium channels (GIRKs), totaling 274 genes.

At least two genes, RGS4 (Unigene cluster Hs 227571) and RGS5 (Unigene cluster Hs 24950) were mapped to the cytogenetic band 1q21-22. In order to determine whether there is altered expression of multiple genes mapped to this locus, a 1q21-22 group was created from genes represented on the microarray locus. The 1999 NCBI database human 1q21-22 map is represented by 70 genes on the microarray, although some of them are not expressed in the central nervous system.

RGS4 Sequences

The RGS4 microarray immobilized probes sequence matched the entry in the NCBI database (accession number U27768, UniGene cluster Hs.227571). Of the 800 bp full-length mRNA, the double-stranded DNA microarray immobilized probe was complementary to the 3' region of 571 nucleotides, as shown in FIG. 1A. The anti-sense, in situ hybridization probe was derived from the mRNA region spanning nucleotides 39–739, resulting in a 700 nucleotide long cRNA probe (see below). The RGS4 cDNA sequence, as determined from the complete mRNA coding sequence is listed as follows:

```
gtacgctcaa agccgaagcc acagctcctc ctgccgcatt tctttcctgc ttgcgaattc   60
caagctgtta aataagatgt gcaaagggct tgcaggtctg ccggcttctt gcttgaggag  120
tgcaaaagat atgaaacatc ggctaggttt cctgctgcaa aaatctgatt cctgtgaaca  180
caattcttcc cacaacaaga aggacaaagt ggttatttgc cagagagtga gccaagagga  240
agtcaagaaa tgggctgaat cactggaaaa cctgattagt catgaatgtg ggctggcagc  300
tttcaaagct ttcttgaagt ctgaatatag tgaggagaat attgacttct ggatcagctg  360
tgaagagtac aagaaaatca aatcaccatc taaactaagt cccaaggcca aaaagatcta  420
```

-continued

```
taatgaattc atctcagtcc aggcaaccaa agaggtgaac ctggattctt gcaccaggga    480
agagacaagc cggaacatgc tagagcctac aataacctgc tttgatgagg cccagaagaa    540
gattttcaac ctgatggaga aggattccta ccgccgcttc ctcaagtctc gattctatct    600
tgatttggtc aacccgtcca gctgtggggc agaaaagcag aaaggagcca agagttcagc    660
agactgtgct tccctggtcc ctcagtgtgc ctaattctca cctgaaggca gagggatgaa    720
atgccaagac tctatgctct ggaaaacctg aggccaaata ttgatctgta ttaagctcca    780
gtgctttatc cacattgtag cctaatattc atgctgcctg ccatgtgtga gtcacttcta    840
cgcataaact agatatagct tttggtgttt gagtgttcat cagggtggga ccccattcca    900
gtccaatttt cctaagtttc tttgagggtt ccatgggagc aaatatctaa ataatggcct    960
ggtaggtctg gattttcaaa gattgttggc agtttcctcc tcccaacagt tttacctcgg   1020
gatggttggt tagtgcatgt cacatgacat ccacatgcac atgtattctg ttggccagca   1080
cgttctccag actctagatg tttagatgag gttgagctat gatatgtgct tgtgtgtatg   1140
tctatgtgta tatattatat atacattaga cacacatata cattatttct gtatatagat   1200
gtctgtgtat acatatgtat gtgtgagtgt atgtatacac acacacacac acacacacac   1260 acactttgc aagagtgatg ggaaagaccc taggtgctca taactagagt atgtgtatgt   1320
acttacatgg gtgttttgat ctctgttctt tcatactaca tttgaacagg caaaatgaa   1380 ctaactgcca tgtaggctaa gaaagaaatg ctaacctgtg gaaagttggt tttgtaaaat   1440
tccatggatc ttgctggaga agcatccaag gaacttcatg cttgatttga ccactgacag   1500
cctccacctt gagcactatt ctaaggagca aataccttag ctcccttgag ctggttttct   1560
ctgatggcac ttttgagctc ctaagctgcc agccttccct tcttttcctg ggtgctcagg   1620
gcatgcttat tagcagctgg gttggtatgg agttggcaga caggatgttc aacttaatga   1680
agaaatacag ctaaggcctt gccagcaaca cctgccgtaa gttactggct gagtgagggc   1740
atagaagtta aaggttactg tttttatcct ctatccttt ttccttcct gatcaaggtg   1800 ctcttctcat tttttcctga gaaccttagc catcagatga ggctccttag tttattgtgg   1860
ttggttgttt tttctttata atggctctgg gctatatgcc tatatttata aaccagcagc   1920 agggaaaga ttatatttta taagagggaa caaattttca caatttgaaa agcccacata   1980
agttttctct tttaaggtag aatcttgtta atttcattcc aaacatcggg gctaacagag   2040
actggaggca tttcttttta ggctctgaga ctaaatgaga ggaaaagaaa agaaaaaaaa   2100
aatgattgtc taaccaattg tgagaattac tgtttgaaac ttttcaaggc acattgaaat   2160
acttgaaaac ttctcatttta tgttatttat gatgttattt tgtacgtgtt attattatta   2220
tattgtttta taaatggagg tacaggatat cacctgaatt attaatgaat gcccaggaag   2280 taatttttctt ctcattcttc taaaactact gcctttcaaa gtgcacacac acgcgtccac   2340
atacactgca ttcgttgctc cagtataaat tacatgcatg agcacctttc tggcttttaa   2400
gccaatataa tgggctgcaa aatgaagaca ccagagtgta tgcatacaaa tctcactgta   2460
ttaaagatgc aggttttcta attgtaccct tcttgtctct ctggcaatct tgcccttaat   2520
atccctggag ttcctcatca gtgtcatttt ctgttataca cagttccaca attttgtctc   2580
tagttgactt caaatgtgta actttattgg tcttgcccta ttataattgt catgactttc   2640
agattgtatc tgaactcaca gactgctgtc ttactaatag gtctggaagg tcacgctgaa   2700
tgagaagtaa attattttat gtaatacatt tttgagtgtg ttttttcagtt gtatttccct   2760 gttatttcat cactatttcc aatggtgagc ttgcctgctc atgctccctg gacagaatac   2820
```

```
tccttcctttt tgcatgcctg tttctatcat gtgcttgata ggcctcaaag ctaatgcttc   2880
cagtgaaaca cacgcatctt aataataagg gtaaataaac gctccatatg aaac          2934
```

For purposes of the present invention, the RGS4 cDNA will be referred to as SEQ ID NO:1.

The 205 amino acid long sequence of RGS4, as determined and reported by Druey et al. in Nature, 379: 742–746 (1996) which is hereby incorporated by reference in its entirety, is listed as GenBank Accession number P49798 as follows:

```
MCKGLAGLPA SCLRSAKDMK HRLGFLLQKS DSCEHNSSHN
KKDKVVICQR VSQEEVKKWA ESLENLISHE CGLAAFKAFL
KSEYSEENID FWISCEEYKK IKSPSKLSPK AKKIYNEFIS
VQATKEVNLD SCTREETSRN MLEPTITCFD EAQKKIFNLM
EKDSYRRFLK SRFYLDLVNP SSCGAEKQKG AKSSADCASL
VPQCA
```

The above amino acid sequence of RGS4 is referred to as SEQ ID NO: 2 for purposes of the present invention.

Untranslated regions upstream and downstream from the RGS4 coding region are identified in the context of the present invention as being relevant components of the RGS4 gene. The RGS4 coding sequence along with these sequences are found on NT_022030 as described in greater detail below. This sequence is

```
agttcaagac cagcctgagc aacatggtga aacccatct ctactaaaaa tacaaaatta    60
gacaggcatg gtgatacacg cctgtaatcc cagctacttc ggaggccgag gcaggagaat  120
cacttgaacc tgctgggggt ggaggttgcg gggagcaaga tcatgccatt gcactccagc  180
ccaggcaaca agagcgaaat gtcatctcag aaaaaaaaaa aggcatttta tatatatata  240
tatatatata tacacacaca cacacatata tatatacaca tatatataca catatataca  300
tatatacaca tatatacaca tatatataca catacatatg tacacatata tatacacata  360
tgtatacaca tatatacaca tatatacaca catatataca catatataca cacatatata  420
cacatatata cacatatata cacatataca catatataca catatataca tatatacaca  480
tatatataat atacacacat atatatacac atatatacac acatatatac acatatatac  540
acatatatat acacatatat acacatatat acatatatac acatatatat acatatatac  600
acatatatac atatatacac atatatacat atacacac atatatacac atacatatac   660
acacacatag atatacatat atacacat atatatacgt atatatatgt atatatatat   720
gctccagagt tcataagagg tagcagttga ttaccactgg ggatagagga aaagagagtt  780
tgacagcagt gtattgtgag aaggacattt caggttgatg gcaaatagta ggggaaatac  840
ataaatgtgt aataaaacct atctgtaagg tagttaagaa ggtaacacta tatatatata  900
tagtgaaagc agtgtaaacc taaaggatgg gccaaggatt taaatgttat agaagaatgg  960
ctaagatgcc aaagctcagt gtatgtggca gaggcatggt gtagggtgtg tccaggttca 1020
tatattgcat taagtgtgag aacaccctgg agtatgaacc aagaaaatgc aaaagccaga 1080
agtgatggag gaaatgagac acaataatga agatattgag aggagggtgt gggcctagag 1140
tgaagctttt cgtgccagta cttcttttga aggcccagtt ctcttctctc tcgggggctc 1200
cttcatctct catagagtcc acagctttta agggccaaca cttgaggtca gcctggctct 1260
ctcatttgag ctggatagaa cattttagag caccatctat tcttcaagag gaagtttaaa 1320
aataaaagaa ccttgaagag gaaaaaatgt agacattcaa tctaaccttt tcattttact 1380
agccaaagct aaatagaatg caggttacct gtttttcagc caggcaccat catttcctaa 1440
ttgttataaa atttattatt attgttgtta ttattattat ttgccataag aagtttccca 1500
```

-continued

```
tatccttta   gtataacaaa   aacacaattc   acaagcatta   taaaacccat   ggtgtctaac   1560
tattaaaaaa  attaagtgga   acacacttgt   cccagctact   ggggaggctg   aggagggagg   1620
atcacgtgat  cccaggggqt   caaggttatg   gagagctatg   attgtgccac   tgcactccag   1680
cctgggtgac  agggaaagac   cctgtctcta   aatttttttt  taaaaaaact   aaactggttt   1740
tattacagag  attctggaga   cagctacaca   taaaagggtg   gtatgcctca   tattagctac   1800
ccagggaggt  ggaatgccaa   cttaggtggt   gtcaccacta   ttaaaaatgc   cccaaagcaa   1860
tcaaaactga  gaacttcctg   ggagcttagc   attgtgcaaa   agcagcacaa   aacacttaaa   1920
caattcacag  ttgtgttgga   atgggaaggc   ctggaaatat   aaaccaaaga   gtatattgtc   1980
taaattgata  gagattacaa   ttgcctgaaa   gaaaagttg   acttttaact   agaatgttca    2040
gagtaggttt  acagaagaag   ctcttaaact   gggctccagt   ggatttgtca   atgctttgga   2100
agctggtggg  gtgggagggt   tggaggggqc   ataaaagtc   atgttggtat   gctctgctca    2160
agtctccatt  ctgtttcctt   ttcctctttt   caatgtcatg   tcccattatt   tcattatggg   2220
cttcccttta  tccaggatca   atatgccacc   tcttggttgt   cttttaccta   cttctccacc   2280
tcactatgga  atcgtccttg   ggtagctcct   gtgcttggga   acctgcacgg   gcacttttct   2340
gatgtcttga  ttccagcttt   actcctaaaa   cttaaatgct   gaggggccaa   caccatggca   2400
gtggtaggga  tgggaatggg   ggtcttgtaa   cacactacat   aaactacacg   aaataaacta   2460
catgaaactc  aacatgtttg   caagactcag   ttcacatcca   tgaggagctc   atgcttctcc   2520
ctcctgctcc  cctagcacac   atgattatct   ctatttggaa   atgttttgca   ttttggtga    2580
agtgaatggt  tcaataactt   tctccaccat   cagaacaaaa   gctctttaag   gttagggatg   2640
ggatcataca  cacttccctt   gtccaagtcc   ccatcaccccc  ttatctagac  aattgctaca   2700
gtttcctaca  cactcttcta   acctcttgca   gtctattttc   ataaaacagc   tagagaactt   2760
tgagatgtaa  gtcaaaaaat   agaacatgtc   gctctttccc   attgtttttg   aaataaagtt   2820
caacccccctt accagggtca   acaaggccct   gcaatgattt   ggtcctgtta   aaaattcttt   2880
agccttaact  catgctgttc   ttccttacac   tcactgcatt   ctagccattg   aggtttctat   2940
gcatcaaact  ttttttggtc   ccagcactgt   gcacatcctt   ctgggtagaa   tgccccttga   3000
tttgtataat  tagcacctcc   ttcatcattt   aggtcttagt   ataactacta   ccttcttaga   3060
gaagctctgc  ttcttcatcc   tataaaaaag   taaaattcct   taccctgtta   ttttttaagt   3120
catccgtgtt  tcattctgtt   aaagttctta   tcacaattta   tcattatttt   atttacagtc   3180
atgtgccaca  taacaatgtt   tcagtcaggg   atagaacaca   aatgtatctg   gccccataat   3240
attataagct  gagaaatttc   tattaactag   tgatatcgca   gccatcataa   gtgtaatgca   3300
ggacattacc  ttttctatgt   ttagatatgt   tagatacaca   aatatatttc   attgtgttat   3360
aatttcctac  agtattcagt   acagtaacat   gctgtacagg   tttgtaacct   aggagtaata   3420
ggctatacca  tacagcttag   gtgtgtagta   ggctataacc   atctaggttt   gtgtaagtac   3480
attctatgat  attcccacaa   tgatgaaatc   acctaactac   acatttctca   gaatgtttca   3540
ctgttgtgaa  gtgacccatg   actatatttt   cctatatact   tgatattttt   gtgcatctgc   3600
ccatgagaat  gtagtgtaag   atcaaaggat   gcaagaatgg   gttctatcca   gtatagtacc   3660
cactacactg  gtgcatgtca   atatgtattt   gttagattaa   tatctcaaga   atgagcacct   3720
ttctcagaca  cataaaagat   gctcaatata   aaagtttgtt   gaactgaacg   ttattggcaa   3780
atgtaacatg  atcggattta   aagaggagcg   aaacagaggt   ctggctcaaa   caccatactt   3840
ctagagtgca  taagaggtag   cagttgatta   ccactggcga   caggagaaaa   aagagcttga   3900
```

-continued

```
ccgcagggta ctgtgaagac atttcaggtt gatggcacag aacaggggaa atacataaat   3960
gtgtgggaat attcagtggt ctgggatgac tacatagtag aatataatga agaaaagagt   4020
ggaagggaaa gatgaaaagt tggaatgggg atgaattatg aaagtaccag aatgttatgc   4080
taaggaatct agatttttaaa atgtgagggc aaattgaagt cctgggcacg ttacaaaact   4140
agaggtcata aagtttaccc taatttacca agatttccta gaggatctat aattggaatc   4200
cagatctgcc tctctgtaaa gttcaagcac tttccatgac accatactgt ttctttccac   4260
ctgcacaatg caaatgaact cttatgaaac tgctgtttct atcctgggct aaatgttgca   4320
gaaaaaagat ttaatctttg ggataaggct atttttgggtt ttctcctact tcttgggaaa   4380
caaggttttc ttcccctggc taattaagtg tggtattgtt cttccaggga atcagtgat   4440 gcatcacctg ctgctatcaa atgtcagggt tggagttcct gatttattgc atgtgcccac   4500
aaagcttggt gcaaagaatt ggacacattt cccaaaagta agacatactg ggaagtccct   4560
gtttaccttc ctggtataca gcatcctcca gccccatatc tttgcttttt agtcctaaaa   4620
atcaataact gaactctcat tgatgtctag gccattgtag taaacaataa agaaggaggg   4680
aggcttctga caactgagag gaaattgtca tctgaagtgg tgcaagcaca gcctgggggct  4740 gagccttggc ctacatcctg cccaagtgga ggatcagtgc cccatttaac atctggtaga   4800
actaaagaac gcaacgcctg ccacaatgac ttatttccct gcatttgata ccgtcaatcc   4860
ttgagaaatg ttttcttttg ttctccctga gcaaaggttg gaaaaatttg aaatttacct   4920
agagaccaca catagttcac atcctgctgt gtggctgaat gtctgccccc cagtaggaaa   4980
cagttcttct aaagcctatt gtcaacaata ccttccagat gttagcattt tacaatttaa   5040
ggaacttaaa atagccttca aactttttgc cagtttctct gatatccaat ctattctttt   5100
actctgcctc ccaagctttc tttctagaat gctaacctga tcggcttaag tacttgaact   5160
acctcttctc ctccattaac tacagagtaa attctggtct tcagagtaac aagaaacacc   5220
ctttagttct cagcatattc gtgcaccttc atttatctct ccttctctct caaagctgca   5280
gtaggggtga aaacgtgtga tacatttttct cttccatcat aagggtcgca accaaaactc   5340
ctatagtaaa agacaggtta ataagagcaa aacctaacaa atttatttaa tcaaagtttt   5400
acatgacatg ggagtcttca gaaatgaaga cccaaagacc cagggggaaac tgtctgtttt   5460 ttttgctgag gttcgatgaa gaatggatag catgtagcca tgtagattag acaaaaggat   5520
atgatctagt ggtaaaggac tcaggggaa acacagcaag gcctgtctat tcagattctt   5580
cttgatctct ctctctctat gtatagcatt cttttcctcct gagtatgggg caggactctt   5640
cttcaatgag ggtcttcaag ggagaaggga gaaagtggcc ttttttagatt ttatggcttg   5700 cttcggggaa gaggagttct agtttctatg acccatcttg gggaagagga attctggttt   5760
ctgtgacttg ctttcatgaa gaaagaggag taagaggcag gagggcagga gatggtcaga   5820
aagagacttg gctgcttctg agggcttccg ctctccttta gttccaagta cttcttagca   5880
taccaaagca ctatactttg gcatatggtt ttctgagctc taacactgca atcatgctaa   5940
actcctctat gaccttcaaa cattccactt gcttttattc tttatggttg tgatggcata   6000
gaggtcaata gcaaagaccc tggagtccca ctgtctgagc tggcataaca ttactaccac   6060
ttaatcaatg tgtaagctca ggtaagtact taagtcctct atgcttcatc tgtaaaatga   6120
gaatcattga agaacattct ctcaggatgg atcatgagga ataagtgaat taactggcat   6180
atagtgctta aaccagtgcc ttgctcagtt agtgacagat aaaatcatct gttattactg   6240
tgcccactat tgtgatgctc ttctcttctt tgtacaacga ctacatctct atttatcatt   6300
```

-continued

```
ttagggtctc cttgtgaaaa accactccag attcaaaaga ttgagtttaa tctctatcct   6360
ctgtgctttc ctggagtttt gtaaagtaaa tcttcacttg acatcatgga taggttcttg   6420
gaaactacaa cttcaagtga aaggacataa ctaaaccaat ttttttctca tcaacgttat   6480
aatgaaatgg cattgatgaa atgatggcat tcaaggacct gctgtaccTt gtttcactta   6540
aagtcactgt ttccaataat ctattgatga cattgaggac ttactatata ataataaata   6600
tatatataat cgacgaaaca ggaatcaaac tgctaactct gctaactggt ctccctgctt   6660
ccacactctg cccactcatc tcagtctttc tttcacaaga gtcagaatga tcagatgaga   6720
cccctcctct gcttctgttt cttccatgga tttccactgc actctgataa agtccagcct   6780
cttgaccaca gcctacaaat ccttgcacga tctatcgttt acttttccat ctccttttat   6840
gctactttca tcttgttctc aattctctag ctatgctggc cccttcttgt tctttcccat   6900 tttttttaa ttttttaaaat ttgtatatat ttatgggtta taagtgaaat cttttttagat   6960 gcataggttg tatagtgata aaatcagggc ttttagggta ttcatcacct gaatgatgta   7020
cattgtaccc cttaagtaat ttctcaccat ccgctgactt cttgccccct gggtattcat   7080
cacctgaatg atgtgcattg taccccttaa gtaatttctc accatccgct gacttcttgc   7140
cccctgggta ttcatcacct gaatgatgtg cattgtaccc cttaagtaat ttctcaccat   7200
ccgctgactt cttgccccct catccttctg aggctccatt gtccatcatt ccacactcta   7260
catctatgtg tacacattat ttagctccta cttataagtg ataacatgca atatttgtct   7320
ttctgtgtct gtcttgtttt acttatgata atggccccca gttctatcta ggctgctgca   7380
aaaggcatga tttcattctt ttttatggct atgttctttc ccaatttaga taaagaacac   7440
tcgcacttgc tcttacttct atttggaata ctaattccta ggcttcttgc attgcttttct   7500 ccttctcacc catcaaatct cattttagat accacctctt caaagagggc tttcctgacc   7560
accttggctg aattagccct tcaccatctg attactctct agcacatcac ctgcccattt   7620
tattcatggt acaggtcaaa atctggaatc acctgatttg tttattttct gactccttct   7680
actgagatga aaactctact agagcggaga ttttatctgc ttgtatcagg tactgcttca   7740
aacagcacct gatacagagt aggtggtcaa aagatatttc ttaaacaaat gaacaaataa   7800
aaagtagatc ttttgagagt aaagctcttc cacactacca gagtcattca ggaatgacaa   7860
atcatagaat aacagaattt gatgctttgt gcatatcaga gaaagaaggt ggaaggttgt   7920
caaggtatca tgatgtacca gtcctcgcct cctcaaacac aatctgcaag tcccacagtg   7980
aaaaagtaag ttaactcatg tgaagcgttt tacaaacact ttttttaaaag tcttaaaact   8040 cctaagaaag caagatttaa tagtcaaaga agtgagtaaa catgaaatgc ctgaacagag   8100
taatgagcta agcacaaagt tagagacatg ttagttaata tgtcttgaaa gcagcagctc   8160
ctgctttcaa ggagcaagaa caaattgggc aagtgaacac tccttgaata aaatgtgtaa   8220
aattaatttt gggttatgtt ctatactgtg tataatagaa tgataaaaat tatttgacta   8280
gcactttgta gtttagaaat atctctattt acacagttta ccttatttga taagactgtt   8340
gagtgatggg atagcatggt ggacaatcca cataactgag tatcgagaca cctgtatctg   8400
gacccagctc tgttagtaag aagctgtaac ctcagcaagt cactttctct ttctgggtct   8460
ctatttcctt tttggtgaaa tgagagtgtt aggctagatt gcctttgaag tcccattttg   8520
tctttaaagt cccatctatt gcagtgattt atatttaact catgacaaat caggcttctc   8580
ttattctaag tgcaagacat aaaactttta ttgtggaatt tcaggcatca gtaaatcttt   8640
ttgggtactc acttatgttc ctgaaatcaa tctatttgag tgatcactct tttaggtgcc   8700
```

-continued

```
caggtaaaca aagaaggcca tggtctttct ttgagtgacc ttctttccct tttaattagt   8760
ctgacctctt taatgtcagt tctgactgat tcatttccct ggtccatctt ccttggtctg   8820
agggccttcc tagtttcata ttgcacttca gttccttcca caccaccatc aaggatggct   8880
gtcaacattc atttgttcta tgttataatt caaggaaaag ttgcccagta gctaatccaa   8940
taaatgccct cttatgggcg gctagagact ttttcctata atttaaatgc atcttctgta   9000
gattatggtc cctccaccac tttacatttg tctgctgtct ccttgctctg ctagtcatgg   9060
aacgtgttgg tagtggggc agtgtgggat gttcaagggc acgtattggg tagggccaca    9120
tatgggcatt gctttgtgcc attctttcta tattttggt attttgcatc tcactggaac    9180
ccaactattt ttcatctctt ccacctaaac tatttgatgc ctctgtttct tatatataaa   9240
gtatagctca ctgtagccta tgatcaggaa cctatctgct ttcaaatga aagctgtttt    9300 ggtcagatct agcaattaat tcccttcttc cacttatagc tttcctctgt aactctggtg   9360
taggtatttg gttatggct ataagatgtg aaacacctga atgattctgt ccatgcaggc    9420
atttcagttc atgatattgt atgtaaaaga tactgattgt ctaggtgttc agaaacacct   9480 ataggctta atattcttac aatcagtttg aaggctggtg atacgcaaag caaactacat    9540 attttctgc ctgctctctc tctttctctc tacatctctc tttctttatc ttttgaaata    9600
tcagtttgga gacttagaat tacataagac ataaacccat ttgatataag aattgctgtg   9660
tatatttgct catctactcc ctcctttggt cctcgagctg ccggtttaga cttttacag    9720 gacgcaggca tgtgaaggag aaactgtcag tgctaggctg aattctgttg ttaccaagat   9780
ttctagaaaa gtattcctca gtcaggttga ttacagatat agcaaatcta ttttcctag    9840 ggtagtttct gtatgctgcc gggcttataa ctgtctgtca tccagctatt tctctccacc   9900
ttcttgtttg cataacaacc aaggcaactt ccgcaaatca ctgcgtggag acgatgatcc   9960
tgccagctcc cttttggaaa tcgtgaggat cagatcttgg accatgtata atatgatgct  10020
tctaatccaa aagaggaaag gcattgggag tcagctccta agtaagctcc agaattcctg  10080
ctggtacttt tccttccagg aagcaacttc cttgatattt ttttttttaca ggcatatgaa  10140 taaaaactat attttgcagc attgtacact tttttttcctt ttctagaaat tctaaacctc  10200
tgacattggt ggagacattg agtacatttt ttcccatatc cctacttttc agaaggattt  10260
tctctgctcg ttcacttaac attgctgatg cgtcagtctt ttcttcctca tctctttcag  10320
gggctggaga ggcagaggga gacagaggag ctggtactgc agagcggtcg tctgattggc  10380
tggacggtcg tagctgggct ataaaagaga ccccctacagg cttagcagga agacgctcag  10440
aggattctga caatatcttt accggagaag aggcaaagta cgctcaaagc cgaagccaca  10500
gctcctcctg ccgcatttct ttcctgcttg cgaattccaa gctgttaaat aagatgtgca  10560
aagggcttgc aggtctgccg gcttcttgct tgaggaggta agattgcttt cagccattaa  10620
ccatattaaa cttttggcta gactttctca gttatttaca tgttgtactt actaacctag  10680
ttctgtgcaa ttagaaacag tgtggtcagg agagcacgac tttctaactt tcctccaaga  10740
ctagctagat attgtgactt aagacatgtg ctccccaaat ttcagcccttt atgtgttgtt  10800 ttgtgtgacc tcagttttga gaactgttct attctttaag ccaggtctaa gaaagctagt  10860
tttaattaag aagcgagatg aggtttgagg ctatgtacag tgatctgtaa tatctccatc  10920
tgtgattact actgctattt gagcatccct ggagtacata gaagcctggc tctgggcttt  10980
ctgattgtat gctacaactt gtttcaggaa aggtacccca gaatgaggtt tggctccatc  11040
atcagaaagg cactatgctt tccgtgtggt ggtgcagtaa cttttcactct ctatgttctt  11100
```

-continued

```
ataagcaaat gttacaatga gatatgagtt ttaaagccag atcttcctta tctctctgcc   11160
ccatctctag ttcttgaagt gtctcatatg agtttggttg agaaatattg atcattacaa   11220
atcagttaat agttttgtag aagatctcat cttaaagaca ttgttttgtt aatatactcc   11280
cttgattttt ttaaaagacc ttacagacat acagctattc atttgttttt ggtttgttca   11340
aaaaaggtat aaagaaatgc attcagaaaa agatcatata ttagccagtt gaaaattaaa   11400
cacaaaatga gtgcatatta cattacttaa tcttgcagtc aaaggtaaaa agtcaaccta   11460
aaggtatact acctgctttc ttatcgcact gcaaatagaa attaccacaa attttatttt   11520
ggaaataatc tcagaaaaca taatttttta tgtactatta aaacatttac tttccaaata   11580
ttctgtcatt caggagtatg gaagtatcga tggcttcttt aaaatgaagc aggagggtct   11640
ggcagagagt atctatgaaa taagttcctc tgaccttcac gcttaatttt ctgaatggag   11700
tggagcaaat tacttcaagc ttcacttaac ttgcatatga aatgaaccgt acaaaaatac   11760
aagagtgtca ggagaaagtt atgctctggt aatattttg caaaacagat aaaagataat   11820
actagagctc tgtcctcaaa gagttaagca gctaatctaa ggaggtaaac tctatgtcag   11880
caggatgaac tgctcttccc tttcctcctc aataaattgc aaatcatcta gtccaacatc   11940
tttaccacca gtgcctgagg ctccagagga gccattgcct tctcaaggtc acataggtgg   12000
tgggtgagtt aggaccaaat ctagaattcc tgactccagt aacttctgaa gtcattttgt   12060
tttttatttt tatggttttta ttataagaat acttgctaag cacacttacc ccctgcattg   12120
attaataact ctaggatctc aggtggatcc agcacataga aatatgaatt cgtttctatt   12180
tggacttcat gatatattta cattatcacc ttggaatcac cctaacattc aggattgtat   12240
cttgttataa tcaaaaagga tgttgcatcc cctgaacagt catcagtcag ggaagcagag   12300
gagggaaagt aatcttgcga ggaagagaaa atactattta agggacagtc agagaacata   12360
atggaattca aactttctgg gaaaacctac atacataaat gtattagtgg ccatcctaaa   12420
tgtctttata tctttgaggc tttatttttcc ctactccaaa tagacacatt tagttattca   12480
tttcttttaa aatggtattt ctcttttttaa actatttctt gactttttta ataaaaagag   12540
atgcaagcaa gaggatattt aataaaaagt aagagagttg agcttaaggc ttattaaaag   12600
acccccttttt tctagttagt caggagctct aatgtgccct ggctacctat taaatggtgg   12660
caataaactg gaagctcagt gatgactcta gcctgcttct cctaatagct gttaagcctc   12720
aaatgccctt tagagtgtgt atgtccttta aagtagctat taagaaggaa agcagcagca   12780
gcagatattg tctagaaaga agccccaaga agctgaggtt tcagcttggg catttgtttt   12840
cgccatccca tgctccattt ccctctgctg gaactgtgca cctcagtgta ttctccctct   12900
atacctcaca gcaggaactg cttgccccccc ccccccccc ccaacataca tggctggaac   12960
tgaatagact tttactttcc cgaggtgctt ctacagttcc ctctgccagc aggggaacag   13020
atggaaatag caatcacctg ccagaaggtg gcgtgcagca aggatgtgca tcttttgccg   13080
ctactgcttt ctgattccta aaaattactc agagatcact catgtgttca gtgattcagg   13140
ttctgttgaa gataccaaag atattcggtt ggtcaaaatg acgggcatat aaaggcttct   13200
caggtttctg aggtaaactg aagggtcaga attccagttg tggatgaagg aaatggtgtt   13260
atgactgcct caaggttttg tagcaagtca tagggaacca agaggaatct tgttttcctc   13320
agaggtcatg ccaactccaa ctcccgttcc ctaaactgtc tctgagccat agactagtaa   13380
```

```
                                      -continued
tggactcttc aagctctacc attaggtatc ttttaaagaa agctggttat tactatttat   13440
tcattttttt ctcttctgtg cagtgcaaaa gatatgaaac atcggctagg tttcctgctg   13500
caaaaatctg attcctgtga acacaattct tcccacaaca agaaggacaa agtggttatt   13560
tgccagaggt aagagaaaag gccttggtga agatgtactt agtattaact atctgatgat   13620
ggggatgttc tgtgagaagg aacttgtgct cctagttaag ccagatttgg atcaagatag   13680
cctccatttt catggagatc ataactacat ttgaaatttc tatacattta gtgaaaaact   13740
gccctcatca ataacatatt ttgtcataac gatggaaaat aaaatctttg ccttcattca   13800
ggatcttaga tttcttgccc caatttttt accatggcat tccaattatt ctgtttctct   13860
ctattttttc tagagtgagc caagaggaag tcaagaaatg ggctgaatca ctggaaaacc   13920
tgattagtca tgaatgtaag tctgacagca acctgggatg aggtactctg ataagacaa   13980 gttatattat gctggtctaa tagaaactgc agcaaggcct ggcttctttc tgatgttcag   14040
actcaggaga ctctttaggt cttaaattca gtctgtttaa aattttaata tgccctagag   14100
ctttgtgata tacaatgaaa agtttatgca ggaaccatgt ggaaaaccat ctctctcatc   14160
acaaggaaaa acggaagaga gaaaaaaaat gataaatatc aataccttct tgcaaaatca   14220
atctcagttt ctcttttccca aattgacctt ggtaattgat agctgcatag gcatttcaga   14280
agcaaaatac ttccttgaaa gaggcttcca acttgagtaa gaatcattag gtagaactgg   14340
gaaccactgg atatcaaaca cagattaggg ttacctgact ccaggtgact tgaaaaaagc   14400
aggggaaaaa gggattgctt gaatccatgc tttatccccc aagtacctca gctttatgtg   14460
aaatagcata tccaagaggc caaccagtgt gatgacaact gtggtccttt ctcctgtatc   14520
ataggtgggc tggcagcttt caaagctttc ttgaagtctg aatatagtga ggagaatatt   14580
gacttctgga tcagctgtga agagtacaag aaaatcaaat caccatctaa actaagtccc   14640
aaggccaaaa agatctataa tgaattcatc tcagtccagg caaccaaaga ggtaggtttt   14700
ttatggatac ataaaaattg tacgtattta tgggagtatgt gtgatatttt gatacatgca   14760
tacaatgtga taacaatcaa atcagggcaa ttgctatata catatctcaa acatttatta   14820
tttctacgtg ttgagaacat tccaaatctc ctcttctagc tatcttaaaa tatacaataa   14880
actattgata actatatcac cctaatgtgc tatcaaacac tagaacctat tccctctacc   14940
caactttcta tctattcctt ctacccatta gccaacctga ccaaaaaggt aagcttttat   15000
ggcagagaac tctctggatc ttagtgaagg ttcctagaat agtggagctg actatcataa   15060
tcttgacaac cccaaataaa tcagttttt aaaaaatctc ttttatccat gtggcttacc   15120
ataacctccc tgcatgaatt tttctgatga atctccccaa tttgttagac agaacagaag   15180
atcttgccct gctctctcta aagcagaaag gttcattctg aacctttcat actctctcac   15240
atgtgccaag gaggacccca atgtcacttt tgttttttgc ttctgaaata cagagggtgc   15300
actgccactt acaagtcact acaaagcata caggcttgca tcctcaacag ggatataggt   15360
ctaatgaagc cttggccttt gccctcagg tgaacctgga ttcttgcacc agggaagaga   15420
caagccggaa catgctagag cctacaataa cctgctttga tgaggcccag aagaagattt   15480
tcaacctgat ggagaaggat tcctaccgcc gcttcctcaa gtctcgattc tatcttgatt   15540
tggtcaaccc gtccagctgt ggggcagaaa agcagaaagg agccaagagt tcagcagact   15600
gtgcttccct ggtccctcag tgtgcctaat tctcacctga aggcagaggg atgaaatgcc   15660
```

-continued

```
aagactctat gctctggaaa acctgaggcc aaatattgat ctgtattaag ctccagtgct   15720
ttatccacat tgtagcctaa tattcatgct gcctgccatg tgtgagtcac ttctacgcat   15780
aaactagata tagcttttgg tgtttgagtg ttcatcaggg tgggacccca ttccagtcca   15840
attttcctaa gtttctttga gggttccatg ggagcaaata tctaaataat ggcctggtag   15900
gtctggattt tcaaagattg ttggcagttt cctcctccca acagttttac ctcgggatgg   15960
ttggttagtg catgtcacat gacatccaca tgcacatgta ttctgttggc cagcacgttc   16020
tccagactct agatgtttag atgaggttga gctatgatat gtgcttgtgt gtatgtctat   16080
gtgtatatat tatatataca ttagacacac atatacatta tttctgtata tagatgtctg   16140
tgtatacata tgtatgtgtg agtgtatgta tacacacaca cacacacaca cacacacact   16200
tttgcaagag tgatgggaaa gaccctaggt gctcataact agagtatgtg tatgtactta   16260
catgggtgtt ttgatctctg ttcttcata ctacatttga acagggcaaa atgaactaac   16320
tgccatgtag gctaagaaag aaatgctaac ctgtggaaag ttggttttgt aaaattccat   16380
ggatcttgct ggagaagcat ccaaggaact tcatgcttga tttgaccact gacagcctcc   16440
accttgagca ctattctaag gagcaaatac cttagctccc ttgagctggt tttctctgat   16500
ggcacttttg agctcctaag ctgccagcct tcccttcttt tcctgggtgc tcagggcatg   16560
cttattagca gctgggttgg tatggagttg gcagacagga tgttcaactt aatgaagaaa   16620
tacagctaag gccttgccag caacacctgc cgtaagttac tggctgagtg agggcataga   16680
agttaaaggt tactgttttt atcctctatc cttttttcct ttcctgatca aggtgctctt   16740
ctcattttt cctgagaacc ttagccatca gatgaggctc cttagtttat tgtggttggt   16800
tgttttttct ttataatggc tctgggctat atgcctatat ttataaacca gcagcagggg   16860
aaagattata ttttataaga gggaacaaat tttcacaatt tgaaaagccc acataagttt   16920
tctcttttaa ggtagaatct tgttaatttc attccaaaca tcgggctaa cagagactgg   16980
aggcatttct ttttaggctc tgagactaaa tgagaggaaa agaaaagaaa aaaaaaatga   17040
ttgtctaacc aattgtgaga attactgttt gaaacttttc aaggcacatt gaaatacttg   17100
aaaacttctc atttatgtta tttatgatgt tattttgtac gtgttattat tattatattg   17160
ttttataaat ggaggtacag gatatcacct gaattattaa tgaatgccca ggaagtaatt   17220
ttcttctcat tcttctaaaa ctactgcctt tcaaagtgca cacacacgcg tccacataca   17280
ctgcattcgt tgctccagta taaattacat gcatgagcac ctttctggct tttaagccaa   17340
tataatgggc tgcaaaatga agacaccaga gtgtatgcat acaaatctca ctgtattaaa   17400
gatgcaggtt ttctaattgt acccttcttg tctctctggc aatcttgccc ttaatatccc   17460
tggagttcct catcagtgtc attttctgtt atacacagtt ccacaatttt gtctctagtt   17520
gacttcaaat gtgtaacttt attggtcttg ccctattata attgtcatga ctttcagatt   17580
gtatctgaac tcacagactg ctgtcttact aataggtctg gaaggtcacg ctgaatgaga   17640
agtaaattat tttatgtaat acatttttga gtgtgttttt cagttgtatt tccctgttat   17700
ttcatcacta tttccaatgg tgagcttgcc tgctcatgct ccctggacag aatactcctt   17760
ccttttgcat gcctgtttct atcatgtgct tgataggcct caaagctaat gcttccagtg   17820
aaacacacgc atcttaataa taagggtaaa taaacgctcc atatgaaact attttgcttgg   17880
aaacacatta atgatccaga gacatgctat gagaaacatc agggtgtagg gtgactttag   17940
```

```
aaaaatactc atactgagtc tttaatccct cctgtgccag tgaactctgg gaaagaaagt    18000
acaaactgaa tattgtttat tctttagttc atgccactgc tctgcttggc tctactcata    18060
gaaccaaggc aatcttagct tcagagactg caaaacagat taagtgattt gcttgcagat    18120
tctcaatcaa ttttcaaggg atagagttca ccttccagag ccattctttt atttccagtt    18180
acccgcctgt ttgagagatg atagagcagt gggaaattga gagagttgaa aggagatata    18240
gattcttacc caaacttcaa aaatccttcc ctccctttg ttaattctct ttcctggaaa     18300
agaggtcata aaatgttcac atcctcagta ataggccctg tgctgtgtct attatgtcat    18360
gagactccca tttcctgacc cttctttccc attgtaagag tagtagttac aaggtgttaa    18420
ggatagatga tcttcaacac ttttgagaaa tagatccatt tacggatctg gtaaaaacta    18480
tggaccgaac catcttttaa gaaaaaaatt cagagaggaa tctaaatttt gtgtgctttg    18540
aggggaaact ctcagaatct cccctcaaaa ctatcattct tctcttatac tatagatgtg    18600
tcagactctc actgggactg tatagttgct gctccctgta tttgataata tctatcaaga    18660
actgcagggt aattcaaagt cacgctatta gcagcaagtg tgagcagtgt tggtttcccc    18720
agtctctaca tccctcatcc tttctttctt ctttatggtt gtctattaaa gaataaaaaa    18780
aaaatattgg ctgaccgttt ttctgaagat aatgtatatc aaggaccacc ttttgaaaaa    18840
cactcattat tcgagaacaa agacacaaca tacgagaatc tctgggatac attcaaagca    18900
gtgtgtagag ggaaatttat agcactaaat gcccacaaga gaaagcagga aagatctaaa    18960
attgataccc taacatcaca attaaaagaa ctagaaaagc aagagcaaac acattcaaaa    19020
gctagcagaa gacaagaaat aactaagatc agagcagaac tgaaggaaat agagacacaa    19080
aaaaccct tc aaaaaattaa tgaatccagg agctggtttt ttgaaaagat taacaaaatt    19140
gatagactgc tagcaagact aataaagaag aaaagagaga agaatcaaat agacacaata    19200
aaaaatgata aaggggatat caccaccgat cccacagaaa tacaaactac catcagaaa    19260
tactataaac acctctacgc aaataaacta gaaaatctag aagaaatgga taaattcctc    19320
gatacataca ccctcccaag accaaaccag gaagaagttg aatctctgaa tagaccaata    19380
acaggctctg aaattgaggc aataatcaat agcttaccaa ccaaaaaaag tccaggacca    19440
gatggattca cagctgaatt ctaccagacg tacaaagagg agctggtacc attccttctg    19500
aaactattcc aatcaataga aaagaggga atcctcccta actcatttta tgaggccagc    19560
atcatcctga taccaaagcc tggcagagac acaaccaaaa aagagaattt tagaccaata    19620
tccttgatga acattgatgc aaaaatcctc aataaaatac tggcaaaccg aatccagcag    19680
cacatcaaaa agcttatcca ccatgatcaa gtgggtttca tccctgggat gcaaggctgg    19740
ttcaacatac gcaaatcaat aaatgtaatc cagcatataa acagaaacaa agacaaaaac    19800
cacatgatta tctcaataga tgcagaaaag gcatttgaca aaatttaaca actcttcatg    19860
ctaaaaactc tcaatcaatt aggtattgat gggacgtatc tcaaaataat aagcactatc    19920
tatgacaaac tcacagccaa tatcatactg aatgggcaaa aactggaagc attccctttg    19980
aaaacgggca caagacaggg atgccctctc tcaccactcc tattcaacat agtgttggaa    20040
gctctggcca gggcaattag gcaggagaag gaaataaagg gtattcaatt aggagaagag    20100
gaagtcaaat tgtccctgtt tgcagatgac atgattgtat atctagaaaa ccccatcgtc    20160
tcagcccaaa atctccttaa gctgataagc aacttcagca aagtctcagg atacaaaatc    20220
aatgtacaaa aatcacaagc actcttatac atcaataaca gacaaacaga gagccaaatc    20280
atgagtgaac tcccattcac                                                20300
```

For purposes of the present invention, this DNA sequence will be referred to as SEQ ID NO:3. The location of the SNPs discussed further below is indicated by bold and larger font letters. Several additional sequences of DNA that are upstream from SEQ ID NO:3 are identified as relevant to the present invention. These DNA sequences are also found on NT_022030 and are

```
ggattaatca tgacaaaagt aatctaaatc tcgttaagac      60
                     tacttaatga tcaatctttc
cctctgtttt ccctgactat agggaagtga attgcccaa      120
                     tccttctcta tcaccccct
gcagccatgc caatgcctta cctctgttat attcagccat     180
                     aggggaagct tattctcata
gaatcagggg ttggcatgta gtcactagct attcttggtg     240
                     agactagtga agatgagtga
aggaaaatat tgcataggtg aaatctcata ggcacaaata     300
                     ggtgtttgtg agagtaacaa
taaaagaaag tcattcccat actctagtag atgactcatt     360
                     ttctcctcat tttttttttt
tcaaggcgtt ctctacaacg gttaacctag taccaaaaat     420
                     ccttctcttt tttcttggac
aaatcctgtt caagttagca tggcatttac tacgtccaag     480
                     acattgtcca gatgctgtgg
```

For purposes of the present invention, this DNA sequence will be referred to as SEQ ID NO:4.

```
agagaaagaa aggcaggcag caaggagaaa aaacattttt      60
                     taaaaaaaga aaattaaaat
ccatgtaatg tctgatatct gttctgctgt atgtgtagat     120
                     ctttccatat accaactcat
tagccttatt ttacaggtga ggaaaatgag accgagagtc     180
                     cttcttactt gaccaagttc
acacagcaag atcacacatg gtagaaccaa tgttagaacc     240
                     taggtgtata cttgctcatt
caatatgtac aataattgca aaagtttcca taggtcttat     300
                     tatatatcag gcactataaa
tgctatgcat gtgtcaacta atttaaacct aagcaatatt     360
                     ataaggaagg tactattata
gaaatctcag ccttacaggt aagggaacag gaataaagag     420
                     atgtgaggta atggcccaag
```

For purposes of the present invention, this DNA sequence will be referred to as SEQ ID NO:5.

```
ataatctcct ttcaagtttt tatcctgtca cttgctagtt      60
                     gtgtgatttg ggacaaatca
tttaactcct tgtaaaggga gagaaggaag gctgtaaaaa     120
                     aattaagtaa taaaaagata
aactccttgt ggtatatttt gttattgttc aaaaatattt     180
                     attgcccctc ttaggatgtc
ttaggtcatt cttgcattgc tataaagaaa tacccaagtc     240
                     tgggtaattt ataaagaata
gaggttaaat tggctcacag ttctgcaggc tgcacaggaa     300
                     gcatcccact ggcgtctact
cacttctggt gaggactcag aaagcttttg cttatgacag     360
                     caggctaagt gagagcaggt
```

For purposes of the present invention, this DNA sequence will be referred to as SEQ ID NO:6.

Several additional sequences of DNA that are downstream from SEQ ID NO:3 are identified as relevant to the present invention. These DNA sequences are also found on NT_022030 and are

```
catggtattt ttactaccca ttgccttcta ggaaagggta      60
                     taacaaatag gaaatattaa
tatttttaat gcctttgagg gtgttaaaaa gcacaactct     120
                     aaggactgtt tgtaaattcc
aggtcaaatg ttgtttctcc ttctctattt cctaccttgg     180
                     tgatggcctg atcttatatg
gagtcactcc aactagaaac cacagaatca tccctagttc     240
                     ctacttctga ctcactccat
acactcaaaa gtcacctgac tctgcagaat ttctctagaa     300
                     aaactctatg aaaacctatt
cctgcctctc cacctgcata gatgtagctt catccaggct     360
                     cttatggtgc atggcctcgg
ttactgcctt atcctttcta ctggcctctc aatctcccat     420
                     ctgataccca ttaatgtact
```

For purposes of the present invention, this DNA sequence will be referred to as SEQ ID NO:7.

```
ccaaatactt tttaggcaca ctgggaagtt acattgtttc      60
                     ttgcaagtga caggttgtcc
tttaattagt tctttctctc aaaaagagac tgctgactcc     120
                     aaactgggaa gaaacccact
caccagcaaa atgctgctga attcactctg atagttttct     180
                     aatctctcat cagtagatga
caataatgaa gccagtattg ttaccacaag actcagatat     240
                     gtctatcacc caagatgatt
tctctttaag acgcaataaa agggaacttt tctccccatt     300
                     tattagcaac taagatgaaa
tgagagccag agaaataaag tgaggaagga aagagaattt     360
                     actaccttta caagctgaaa
```

For purposes of the present invention, this DNA sequence will be referred to as SEQ ID NO:8. In all upstream and downstream sequences (i.e. SEQ ID NOS: 4, 5, 6, 7, and 8), the location of SNPs are indicated by bold and larger font letters.

In Situ Hybridization

Double-stranded cDNA containing the RGS4 sequence was first amplified from normal human brain cDNA using custom designed primers (Forward primer sequence: CCGAAGCCACAGCTCCTC (corresponding to SEQ ID NO: 3); Reverse primer sequence: CATCCCTCTCCCT-TCAGGTG (corresponding to SEQ ID NO: 4), and "touch-down" PCR with AmpliTaq Gold (PE Biosystems): (94° C. for 10 minutes (min), followed by 10 PCR cycles with a high annealing temperature 94° C. for 30 seconds (sec), 62° C. for 30 sec, and 72° C. for 60 sec), 10 cycles with a medium annealing temperature (94° C. for 30 sec, 60° C. for 30 sec, 72° C. for 60 sec), and 20 cycles at a low annealing temperature (94° C. for 30 sec, 58° C. for 30 sec, 72° C. for 60 sec). The product of this touchdown PCR reaction produced a single bright band on a 2% agarose gel and was purified and ligated into a T/A plasmid cloning vector (AdvanTAge, Clontech) and transformed into competent *Escherichia coli* cells and plated overnight at 37° C. Colony PCR was performed on selected colonies containing the insert, and the products of these reactions were restriction digested and sequenced to verify orientation and insert identity.

[$^{35}$S]-labeled riboprobes were synthesized using the T7 Riboprobe In Vitro Transcription System (Promega kit #P1460) and purified using RNeasy kit (Qiagen #74104). A scintillation counter was used to verify the specific radio-activity and yield of the probe. During hybridization, approximately 3 nanograms (ng) of probe was used per slide in a total volume of 90 μl. All other methods used were those described previously in Campbell et al., in Exp. Neurol. 160: 268–278, 1999, which is hereby incorporated by reference.

Tissue blocks containing the regions of interest (PFC area 9, motor cortex [MC] and visual cortex [VC]) were identified using surface landmarks and sulci (the superior frontal gyrus, the central sulcus and precentral gyrus, and the calcarine sulcus, respectively). After histological verification of the regions, 20 μm sections containing these regions were cut with a cryostat at −20° C., mounted onto gelatin-coated glass slides, and stored at −80° C. until use. The slides were coded so that the investigator performing the analysis was blind to the diagnosis of the subjects.

Following hybridization and washing, slides were air dried and exposed to BioMax MR film (Kodak) for 8–22 hours and then dipped in emulsion (NTB-2, Kodak), and exposed for 3–5 days at 4° C. High resolution scans of each film image were used for quantification of signal with Image (Scion Corporation, Fredrick, Maryland), version 4.0b), and darkfield images were captured from the developed slides. Throughout all steps and procedures, subject pairs were processed in parallel. Hybridization of sections with sense RGS4 riboprobe, used as a specificity control, did not result in detectable signal.

Quantification was performed by subtracting the background white matter OD from the average signal OD measured in five non-overlapping rectangular regions on each section (3 sections per tissue block). In PFC and MC, these rectangular regions spanned cortical layers II–VI. Due to the lack of RGS4 signal in layer IV throughout the neocortex, and the great expansion of this layer in VC, the supragranular and infranular signal intensities were analyzed separately in VC. However, there were no significant differences in the levels of signal contained in the supra- and infragranular layers, so they were combined as a measure of overall VC signal intensity.

Each in situ hybridization was repeated three times in separate hybridization reactions. The resulting ODs were background-corrected and averaged. Visual cortex (V1) OD quantification, due to a bi-laminar transcript distribution, was performed separately for the supragranular and infragranular layers.

In order to search for novel candidate genes whose expression is consistently altered in schizophrenia, high-density cDNA microarrays (UniGEM-V, Incyte Genomics) were used to examine the expression patterns of over 7,800 genes and ESTs in post mortem samples of prefrontal cortex area 9 from six matched pairs of schizophrenic and control subjects.

Comparison and Statistical Analyses

Figure 1B:
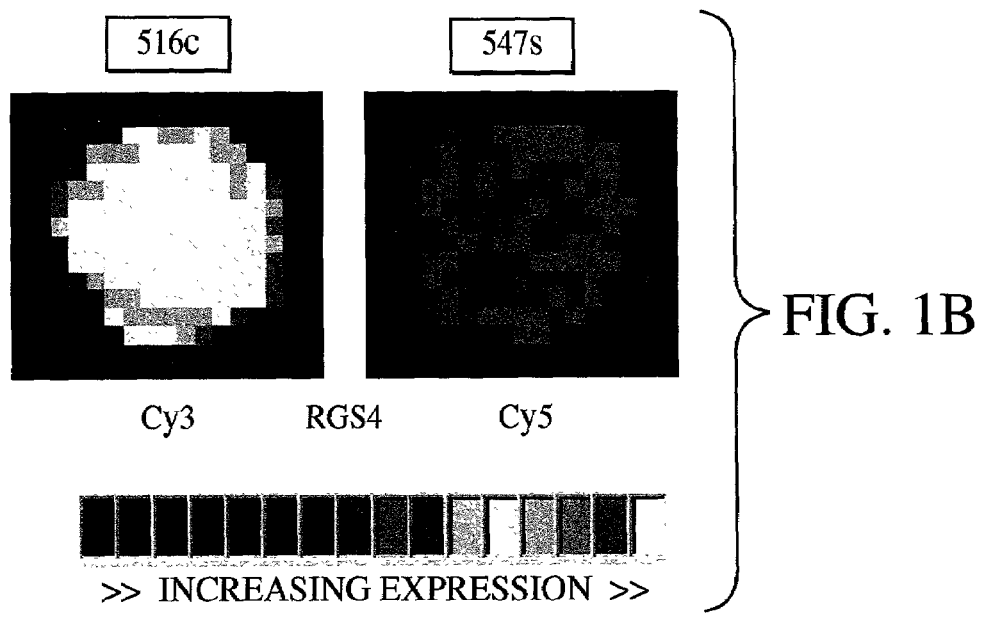
FIG. 1B is a pseudocolored intensity view of a single RGS4 feature from the 516 control/547 schizophrenic PFC comparison after a dual-fluorescent hybridization; both images represent the same spot under cy3 and cy5 excitation, respectively; the balanced cy3 signal intensity α-control subject) was 6.2-fold brighter than the cy5 signal intensity (s-schizophrenic subject)

As illustrated in FIG. 1B, a gene was determined to be expressed if the arrayed immobilized probe or target (the design of which is shown in FIG. 1A) was successfully amplified by PCR, produced a signal from at least 40% of the spot surface and had a signal/background ratio over 5-fold for either the cy3 or cy5 probe. Both images represent the same spot under cy3 and cy5 excitation, respectively. In this experiment, the balanced cy3 signal intensity (control or c-subject) was 6.2-fold brighter than the cy5 signal intensity (schizophrenic or s-subject).

Genes were comparably expressed between the control and experimental samples if the cy3/cy5 ratio or cy5/cy3 ratio was <1.6. Over 80% of observations fell into this class. Gene expression was changed between the two samples at the 95% confidence level (95% CL) if the cy3/cy5 or cy5/cy3 signal was 1.6–1.89. Gene expression was changed between the two samples at the 99% confidence level (99% CL) if the cy3/cy5 or cy5/cy3 signal was 1.9.

In the microarray analyses, data from experimental subjects were compared to data from matched control subjects in a pairwise design to control for the effects of age, race, sex and PMI on gene expression. To evaluate potential changes in gene group expression on the microarrays, two types of statistical measures were employed: 1) $\chi$-square analysis was performed on the distribution of genes in a group versus the distribution of all genes called present on each individual microarray. The distribution of gene expression ratios was divided into five different bins based on confidence levels for individual gene comparisons: <−1.9, −1.89 to −1.6, −1.59 to 1.59, 1.6 to 1.89 and >1.9. 2) A paired t-test (degrees of freedom=5) was used to compare mean expression ratios for a given gene group to the mean expression ratios for all expressed genes across all six subject pairs. A gene group was considered to be changed only if it reported differential expression by both the $\chi$-square and t-test compared to the mean and distribution of all expressed genes. Microarray changes were also analyzed by descriptive statistics and correlation.

To mimic the microarray comparisons, the in situ hybridization data were analyzed using ANCOVA with diagnosis as the main effect, subject pair as a blocking factor, and brain pH and tissue storage time as covariates. Furthermore, to verify that the pairing of subjects adequately controlled for sex, age, and PMI, we also conducted an ANCOVA with diagnosis as a main effect, and sex, age, PMI brain pH, and tissue storage time as covariates. Since both models produced similar results, the values from the ANCOVA with subject pair as a blocking factor are reported. Changes between groups were also analyzed by descriptive statistics, Pearson correlation, and Factor analysis.

Pittsburgh Cases and Parents for Genotyping Analysis

Inpatients and outpatients were recruited at Western Psychiatric Institute and Clinic, a University of Pittsburgh-affiliated tertiary care center and 35 other treatment facilities within a 500 mile radius of Pittsburgh. The Diagnostic Interview for Genetic Studies (DIGS) was the primary source for clinical information for probands (Nurnberger, et al. *Archives of General Psych.* 51, 849–59; discussion 863–4, 1994). Additional information was obtained from available medical records and appropriate relatives, who also provided written informed consent. Consensus diagnoses were established by board certified psychiatrists. There were 93 Caucasian and 70 African-American cases. Genomic DNA, but not clinical information was available from all parents of the Caucasian cases. Cord blood samples were obtained from live births at Pittsburgh and served as unscreened, population-based controls. There were 169 individuals. They included 76 Caucasians and 93 African-Americans.

National Institute of Mental Health Collaborative Genetics Initiative (NIMH CGI) Sample From 1991–98, pedigrees having probands with schizophrenia or schizoaffective disorder, depressed (DSM IV criteria) were ascertained at Columbia University, Harvard University, and Washington University. The DIGS was the primary interview schedule. The families were ascertained if they included two or more affected first degree relatives (Cloninger et al. *Am. J. Med. Gen.* 81, 275–81, 1998, which is hereby incorporated by reference). We selected case-parent trios and available affected siblings from this cohort. Thus, 39 cases, their parents and 30 affected sibling-pairs were obtained. They comprised 25 Caucasian families, 10 who reported African-American ethnicity and 4 from other ethnic groups. Transmission disequilibrium test (TDT) analysis utilized only one case/family.

Written, informed consent was obtained from all participants. Ethnicity was based on self-report (maternal report for neonatal samples).

DNA Sequencing and Polymorphism Detection

The genomic sequence for RGS4 was obtained from NT_022030 (390242 bp), a currently unfinished clone from Human Genome Project, Chromosome 1 database. The annotated data revealed three identified genes, namely, RGS4, $MSTPO_{32}$ and RGS5. The genomic organization of RGS4 and RGS5 includes 5 exons which is typical for the RGS family gene.

A panel of 10 African-American cases and 6 Caucasian controls was initially used to screen for polymorphisms in the exonic, intronic, and flanking genomic sequences of the RGS4 gene. The re-sequenced region included 6.8 kb upstream and 2.9 kb downstream of the coding sequence. The genomic sequence was used to design primers and amplicons ~500 bp were generated, with overlapping sequences. The amplified fragments were sequenced using an ABI 3700 DNA sequencer. The sequencing panel that was used (n=16) has over 80% power to detect SNPs with minor allele frequency over 5% (Kruglyak et al. *Nature Gen.* 27, 234–236, 2001, which is hereby incorporated by reference). We also sequenced cDNA sequences from the post-mortem samples reported on earlier (Mirnics et al. *Mol. Psychiatry* 6, 293–301, 2001). The sequences were aligned using Sequencher (version 4.5) and polymorphisms were numbered consecutively. Additional SNPs localized to NT_022030 were obtained from the NCBI SNP database. We also obtained genotype data from a prior study of the NIMH sample.

Polymorphism Analysis

PCR based assays included primers (5 pmol) with 200 μM dNTP, 1.5 mM MgCl2, 0.5 U of AmpliTaq Polymerase (PE Biosystems), 1× buffer and 60 ng of genomic DNA in 10 or 20 μl reactions. The PCR conditions were 95° C. for 10 min followed by 35 cycles (94° C. for 45 sec, 60° C. 45 sec and 72° C. for 1 min). The final extension at 72° C. for 7 min. The amplified products were digested with restriction endonucleases, electrophoresed on agarose gels, and visualized using ethidium stain. SNPs 4 and 18 were identified as single strand conformational polymorphisms (SSCP) (Orita et al. *DNAS* 86, 2766–70, 1989). All genotypes were read independently by two investigators.

Polymorphisms were detected only in the intronic and flanking sequences of RGS4 (FIG. 6). Among 34 identified SNPs, one was selected from each of six sets which appeared to be in complete linkage disequilibirum in the re-sequenced panel. SNPs were further evaluated for informativeness (minor allele frequency >0.1) and availability of reliable genotyping assays. Among the Caucasian cases from Pittsburgh, deviations from Hardy Weinberg equilibrium (HWE) were noted for SNP 7 (p<0.03) and SNP 13 (p<0.01). Though all maternal genotypes conformed to HWE, deviations were noted at SNPs for the fathers of Pittsburgh cases at SNPs 4 and 18 (p<0.05). For the analysis of IBD sharing among affected sibling-pairs from the NIMH samples, we also used genotypes for markers D1S1595, D1S484, D1S1677, D1S431 and D1S1589 (Faraone et al. *Am. J. of Med. Gen.* 81, 290–5, 1998).

Statistical Analysis

PEDCHECK software was used to check for Mendelian inconsistencies (O'Connell et al. *Am. J. of Hum. Gen.* 63, 259–266, 1998, which is hereby incorporated by reference). $\chi^2$ tests were employed for comparisons between cases and unrelated controls. We also used SNPEM software based on the EM algorithm to estimate and compare haplotype frequencies (Fallin, 2001, which is hereby incorporated by reference). We utilized GENEHUNTER software for TDT analysis of individual SNPs and haplotypes, as well as analysis of identity by descent among affected sibling-pairs (Kruglyak et al. *Am. J. of Hum. Gen.* 58, 1347–63, 1996; Spielman et al. *Am. J. of Hum. Gen.* 54, 559–60, 1994, both of which are hereby incorporated by reference). We also used TRANSMIT for global tests of association involving multiple haplotypes (Clayton et al. *Am. J. of Med. Gen.* 65, 1161–1169, 1999a; Clayton et al. *Am. J. of Hum. Gen.* 65, 1170–1177, 1999b, both of which are hereby incorporated by reference).

Microarray Results

Single gene transcripts were analyzed across all cDNA microarray comparisons. Across the six microarray comparisons over 90,000 data points were collected, and from these 44,000 were expression-positive observations, resulting in an average of 3,735 expressed genes/microarray. Of the expressed transcripts, 4.8% were judged to be differentially expressed (99% CL) between the schizophrenic and control subjects. The observed differences for any subject pair, in general, were comparably distributed in both directions: 2.6% of the genes were expressed at higher levels in schizophrenic subjects than in the matched controls, whereas 2.2% were expressed at lower levels in the schizophrenic subject.

Figure 1C:
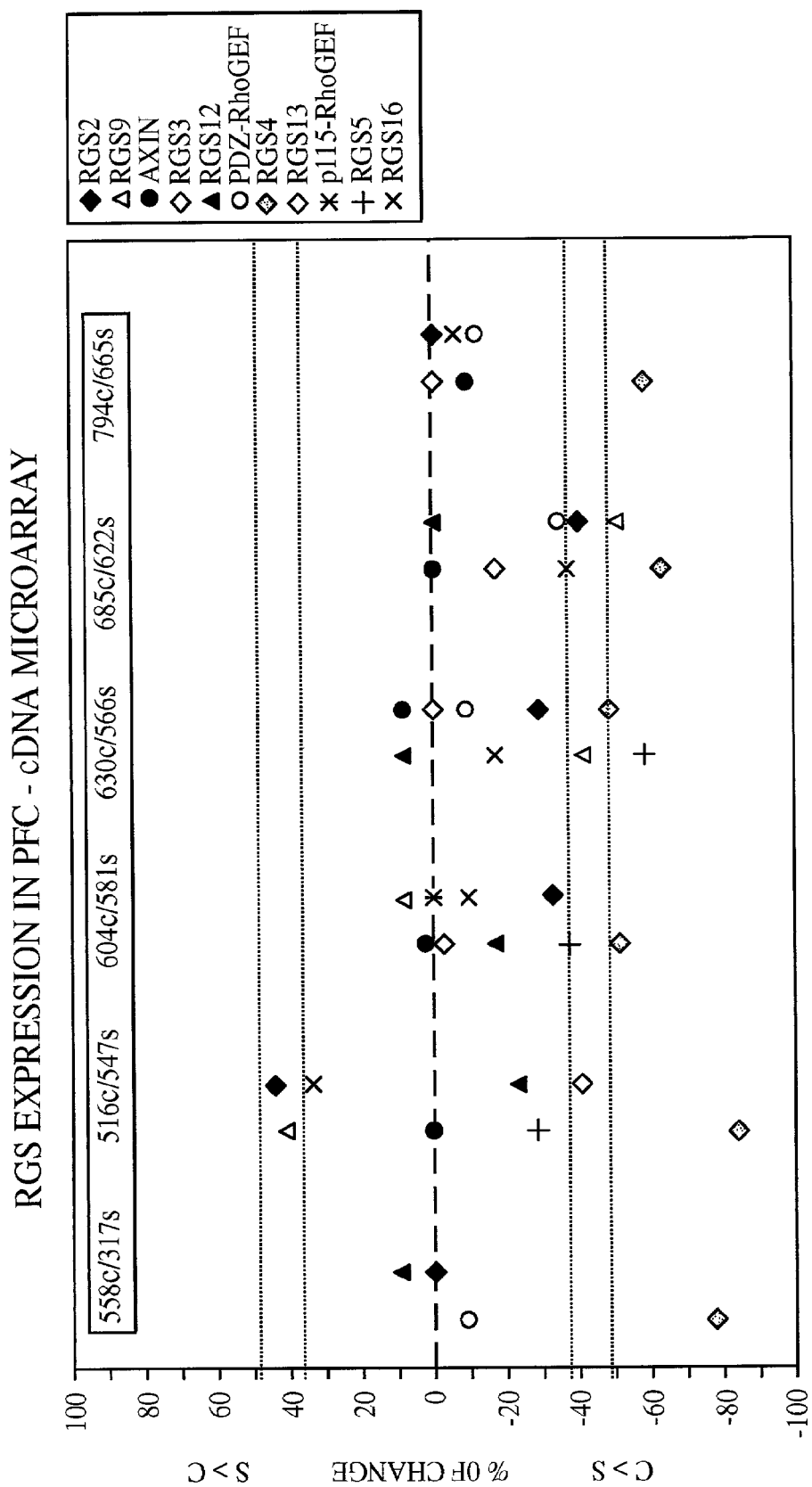
FIG. 1C displays changes in RGS expression in the PFC of schizophrenic and control subjects reported by cDNA microarray analysis.

Of all the expressed genes, RGS4 transcript reported the most significant decrease across all schizophrenic subjects. In fact, it was the only gene decreased at the 99% CL in all microarray comparisons. The microarray-bound, 571 base pair long, double-stranded cDNA immobilized probe corresponded to the 3' end of RGS4 and had a less than 50% sequence homology to any other known transcript, including RGS family members. This high binding specificity, coupled with strong cy3 and cy5 hybridization signal intensities, as shown in FIG. 1B, showed that RGS4 was robustly expressed in the human prefrontal cortex. Across the six microarray comparisons, RGS4 mRNA levels were decreased 50–84% in the PFC of schizophrenic subjects, as illustrated in FIG. 1C, while the expression of the ten other RGS family members represented on the microarray were unchanged in the schizophrenic subjects. In the scatter plot shown in FIG. 1C, the X-axis reports subject pairs, the Y-axis reports percent change between schizophrenic and control subjects. Individual symbols represent a gene expression difference between a schizophrenic and control subject in a single pairwise comparison. The black dashed line denotes equal cy3 and cy5 signal intensity (similar expression) between schizophrenic and control subjects (0% change), green dashed line denotes the 95% confidence interval (37.5% change), red dashed line represents 99% confidence interval (47.5% change). Missing symbols in some pairwise comparisons indicate that the corresponding genes' microarray hybridization did not meet expression criteria. Across all the RGS members represented on the microarray, only RGS4 showed a consistent expression change over the 99% CL in schizophrenic subjects.

To confirm the microarray findings for the RGS4 expression changes, in situ hybridization was performed on the PFC from the same five subject pairs used for the microarray experiments (for pair 794c/665s, no sections were available from the same block of tissue used in the microarray experiment). As a further test of the robustness of the microarray data, five additional subject pairs were added to the in situ hybridization analysis. Radiolabeled cRNA probes designed against RGS4 mRNA were used to localize and quantify relative transcript levels. In the control subjects, RGS4 labeling was heavy in the prefrontal cortex, as shown in FIG. 2A, mimicking previously described labeling in the rat. In the gray matter of prefrontal cortex, the RGS4 riboprobe heavily labeled various size and shape cell profiles, including both projection neurons and interneurons. This labeling was the most prominent in layers III and V, with sparse labeling in the intervening granular layer IV, and appeared to be present over both large pyramidal neurons and smaller cells that could represent interneurons. High power photomicrographs of PFC tissue sections from a schizophrenic (622s) and matched control (685c) subjects were viewed under darkfield illumination. Micrographs for each subject were taken under identical conditions. Roman numbers denote cortical layers. Pial surface is to the left. Strong labeling across all cortical layers except lamina IV was observed, and diminished labeling in the matched schizophrenic subject across all the layers was noted (scale bar=400 μm). White matter labeling was absent.

Figure 2B:
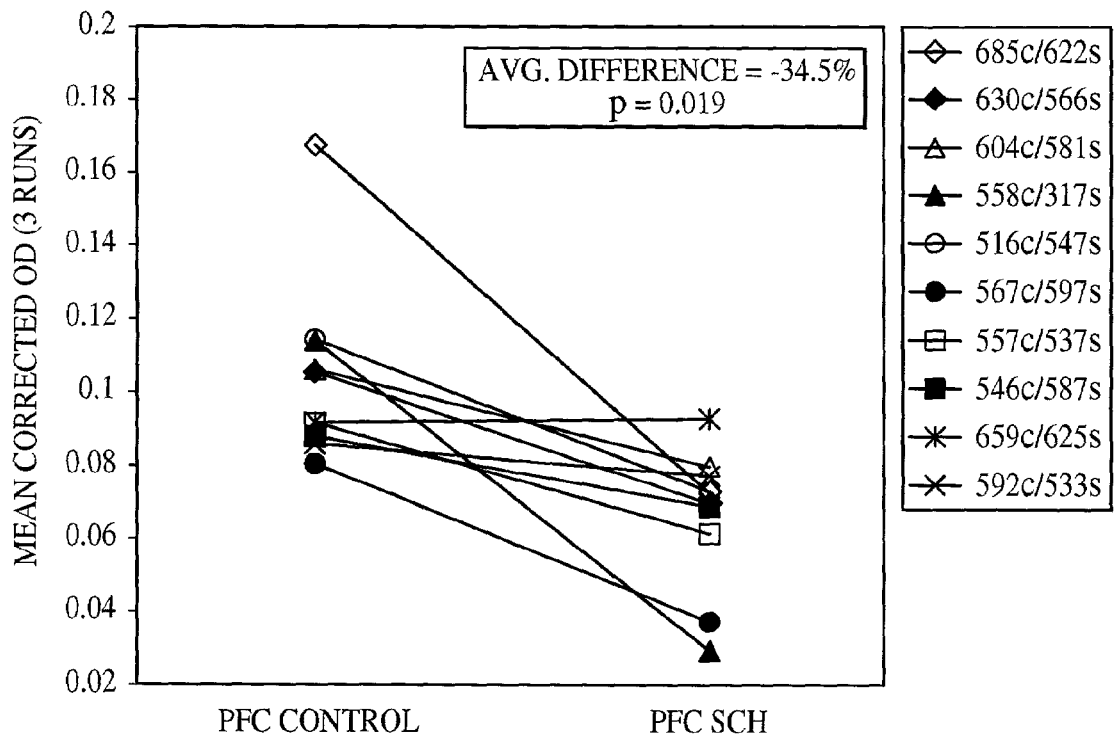
FIG. 2B shows the in situ hybridization data from 10 PFC pairwise comparisons which were quantified using film densitometry.
Figure 2A:
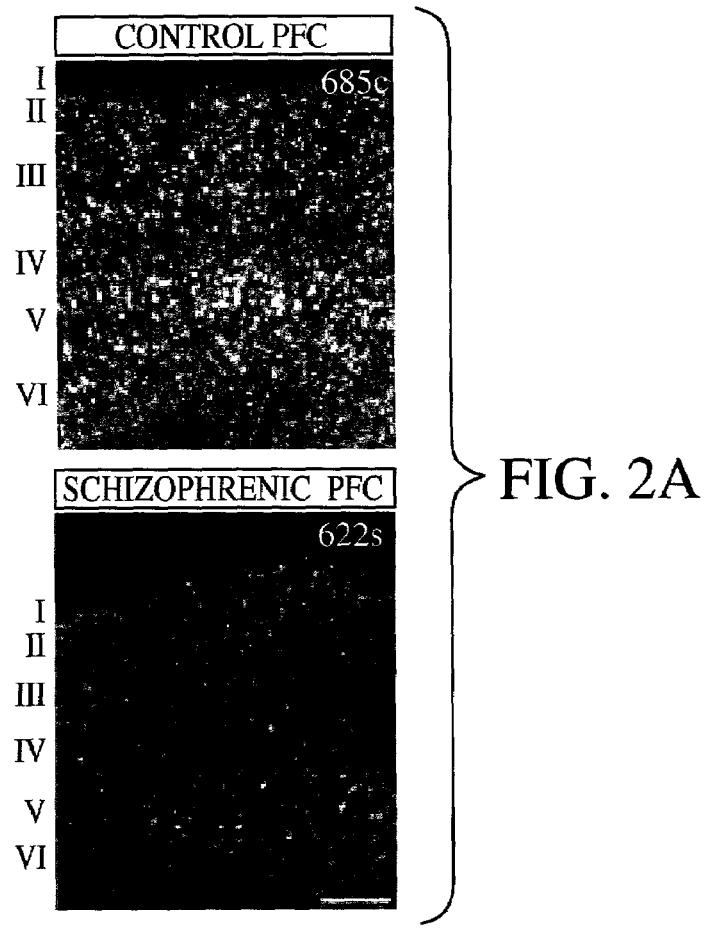
FIG. 2A shows in situ hybridization results for PFC RGS4 expression levels which are decreased in 9 of 10 schizophrenic subjects.

Based on optical density analysis, 9/10 subject pairs exhibited a 10.2% to 74.3% decrease in PFC RGS4 expression, as shown in FIG. 2B. The in situ hybridization data from 10 PFC pairwise comparisons were quantified using film densitometry. The X-axis represents subject classes, the Y-axis reports average film OD from 3 repeated hybridizations, measured across all layers. Lines connecting symbols indicate a matched subject pair. Note that in 10 PFC pairwise comparisons, 9 schizophrenic subjects showed RGS4 transcript reduction (mean=−34.5%; $F_{1,15}$=6.95; p=0.019).

Specificity of RGS4 Expression Changes

To investigate whether RGS4 transcript decrease is a specific alteration in schizophrenia, the same microarray data was analyzed for consistent gene expression changes across other RGS-family members (FIG. 1C). Nine of the eleven RGS family members represented with immobilized probes on the microarrays reported expression in four or more microarray comparisons. RGS13, primarily lung-specific family member, was not expressed in any of the comparisons, while p115-RhoGEF reported expression in only one comparison. RGS4 was the only family member (and the only gene on the microarray) to report a consistent change in expression over the 99% CL in every schizophrenic subject. RGS5 mRNA (a gene also localized to cytogenetic position 1q21-22) was decreased at the 99% CL in one subject pair, at the 95% CL in another subject pair, and unchanged in the remaining 2 pairs that showed detectable RGS5 expression by microarrays. Expression of the other RGS family members did not display any consistent differences across the schizophrenic subjects. The mRNA from pair 567c/537s was analyzed a second time on the newest Incyte microarray, UniGEM-V2, which includes five additional RGS family members (RGSZ, RGS1, RGS7, RGS11, and RGS14). This analysis confirmed that, in the 6 comparisons, RGS4 was the only significantly changed RGS family member.

Heterotrimeric G-proteins, the main substrates for RGS family members, were assessed for expression patterns. Several reports suggest Gα changes associated with schizophrenia. Thus, it was desirable to assess whether the decrease in RGS4 expression correlated with changes in Gα expression levels. Of the eight Gα RGS substrates represented on the microarrays, only $G_o$ expression was changed beyond the 95% CL in three or more pairwise comparisons. These three subjects with increased Go levels (317s, 547s, and 622s) showed the most robust decrease in RGS4 expression both in the PFC microarray and in situ hybridization assays.

Figure 3A:
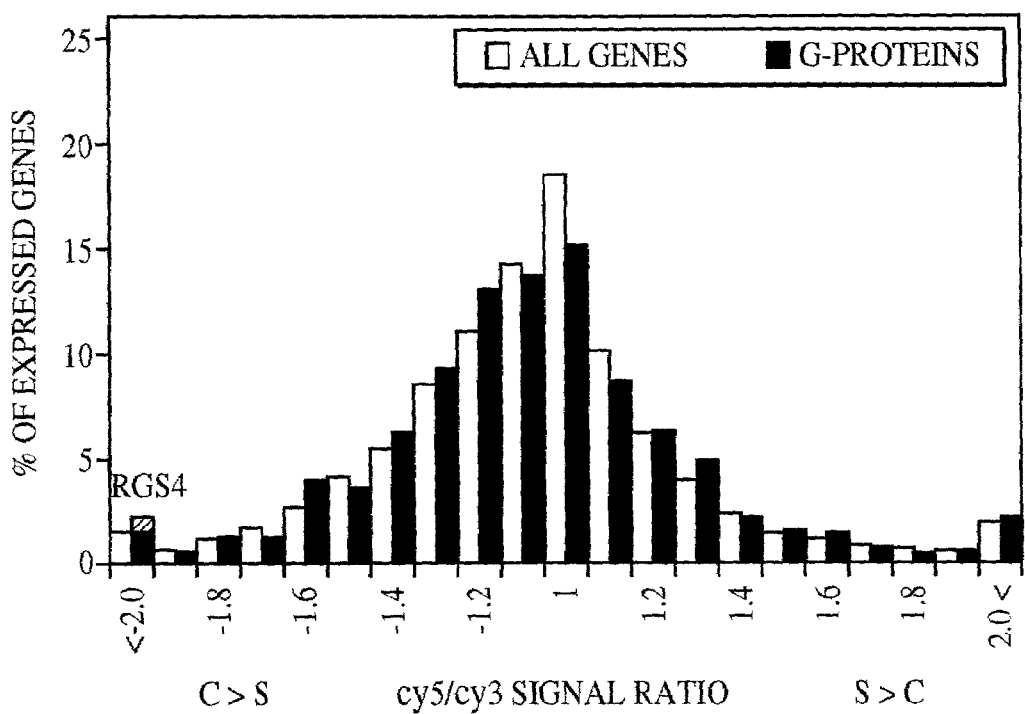
FIG. 3A shows that 632 G-protein signalling-related genes were detected out of 1644 possible detections (274 genes/microarray×six microarrays)
Figure 3B:
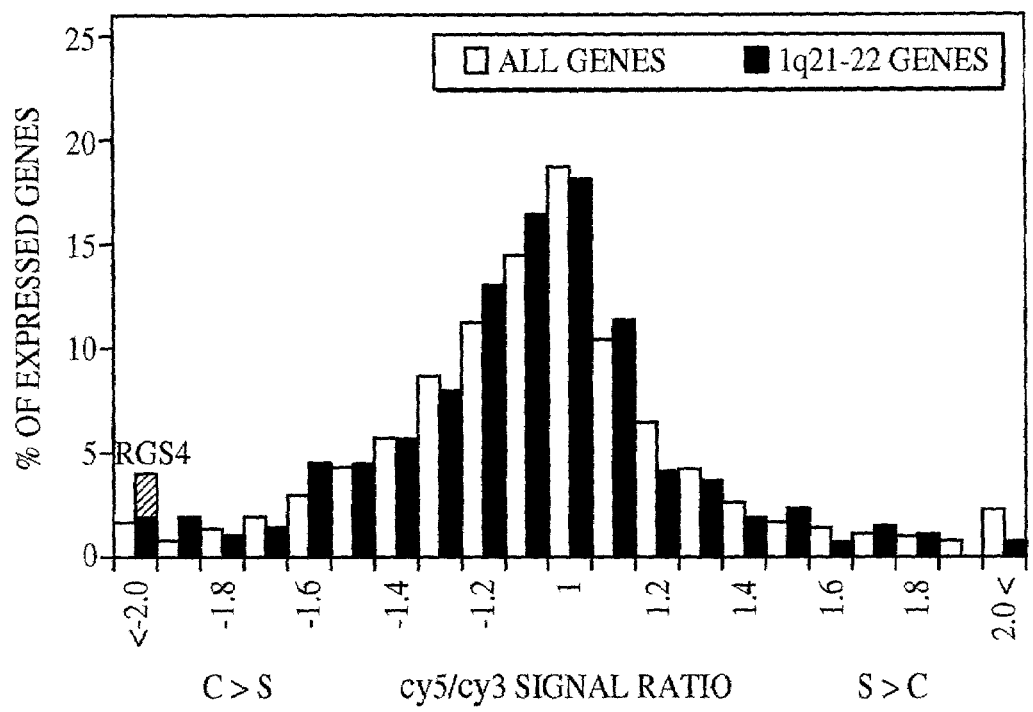
FIG. 3B shows that 239 1q21-22 locus-related genes were detected out of 420 possible detections (70 genes/mircoarray×six microarrays); RGS4 contribution to the transcript distribution is denoted by a hatched bar.

Expression of 274 genes known to be involved in the G-protein signaling cascades (GPCR, heterotrimeric G-proteins, RGS, GIRKS, G-protein receptor kinases, and mitogen-activated protein kinases) were analyzed in a gene group comparison. An average of 105 genes belonging to this group were expressed in each comparison. The results of microarray analyses showing G-protein and 1q21-22 locus-related expression differences in the PFC of six pairs of schizophrenic and control subjects are shown in FIGS. 3A and 3B. For both gene groups, all expressed genes were classified into signal intensity difference intervals (0.1 bins) according to their cy5/cy3 signal ratio. Transcripts in a "1" bin had identical cy5 vs. cy3 signal intensities. Positive values (to the right) on the X-axis denote higher cy5 signal in schizophrenic subjects (S>C), negative values (to the left) correspond to higher cy3 signal intensity in the control subjects (C>S). The Y-axis reports percentage of expressed genes across the six subject pairs per bin for each gene group. In both panels, the white bars (All genes) denote distribution of all expressed genes across the six PFC pairwise comparisons (n=22,408). Additionally, in both panels, RGS4 contribution to the transcript distribution is denoted by a hatched bar. Note that in both FIG. 3A and FIG. 3B, the cy3/cy5 signal distribution of G-protein and 1q21-22 gene groups was comparable to the distribution of all expressed genes across the six microarray comparisons.

At the 99% confidence level, 5.6% of G-proteins showed a different distribution between schizophrenic and control subjects, as shown in FIG. 3A: 2.8% of G-proteins were decreased, while 2.8% were increased in the PFC of schizophrenic subjects. Of the 2.8% decrease in schizophrenic subjects, RGS4 observations alone accounted for nearly half of the decrease. When RGS4 was removed from the G-protein group, a gene group analysis by $\chi^2$ test and t-test closely matched the distribution of all expressed genes, suggesting that the majority of different expression levels can be attributed to normal human variability. Except RGS4, no other member of the G-protein gene group was consistently changed across the subject pairs over the 95% or 99% confidence levels.

The RGS4 gene has been mapped to locus 1q21-22, a novel schizophrenia locus recently implicated by pedigree studies with a linkage of disease score (LOD) of 6.5 as described by Brzustowicz et al. supra. To address if any other genes at this locus displayed altered expression in the PFC of schizophrenic subjects, 70 additional transcripts originating from this cytogenetic region were analyzed. At the 99% CL, 0.4% of 1q21-22 genes were increased, and 5.9% were decreased in the schizophrenic subjects. Of the transcripts decreased in schizophrenic subjects, RGS4 observations alone accounted for nearly half of the decreases, as shown in FIG. 3B. Furthermore, of all the genes on the 1q21-22 locus, only RGS4 showed a consistent expression change across all the pairwise comparisons over the 95% or 99% confidence levels. Of the remaining genes on this locus, only the ALL1-FUSED gene (AF1q GenBank Accesion #U16954) reported consistent expression change over the 95% CL in the schizophrenic subjects in three or more pairwise comparisons. Furthermore, as a gene group, the expression of the remaining genes on locus 1q21-22 showed the same overall pattern as genes located on non-schizophrenia loci or the overall average gene expression which is shown in FIG. 3B.

Regional RGS4 Gene Expression Changes

Figure 4A:
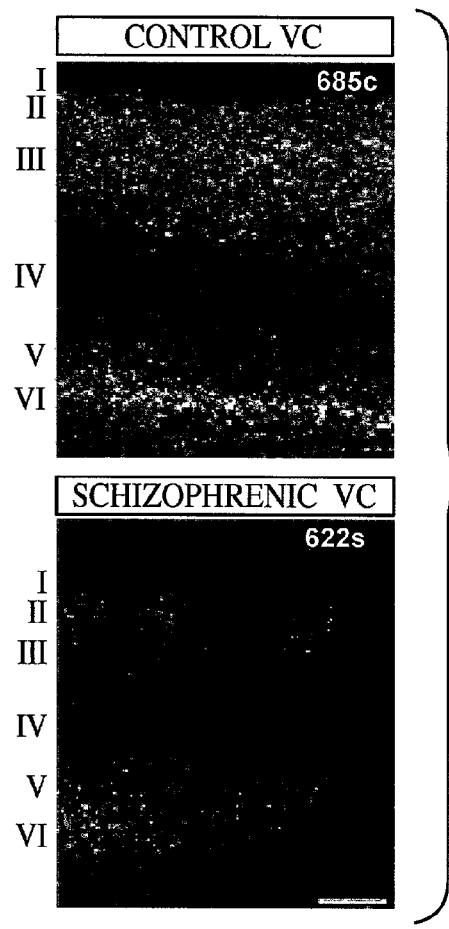
FIG. 4A shows high power photomicrographs of VC tissue sections from the same matched pair of schizophrenic and matched control subjects represented in FIG. 2A, viewed under darkfield illumination.

To test whether RGS4 transcript decrease is specific to the prefrontal cortex or includes a more widespread cortical deficiency, RGS4 expression was assessed by in situ hybridization in the visual cortex (VC) and motor cortex (MC) from the same 10 pairs of control and schizophrenic subjects (for pair 558c/317s MC material was not available, and this pair was substituted with pair 794c/665s). The figure layout for FIGS. 4A–D is similar to that of FIGS. 2A–B. In VC, RGS4 in situ hybridization showed heavy labeling under darkfield illumination of diverse cell population in the gray matter, with a very prominent bi-laminar labeling pattern in the supragranular and infragranular layers, as shown in FIG. 4A. Roman numbers denote cortical layers, scale bar=400 µm. There was very sparse labeling in the well-developed layer IV, with very few cellular elements exhibiting detectable levels of RGS4 mRNA. These high power photomicrographs show that RGS4 levels are significantly decreased in the VC region of the schizophrenic subjects. The OD measurements on these two layers were performed separately.

Figure 4C:
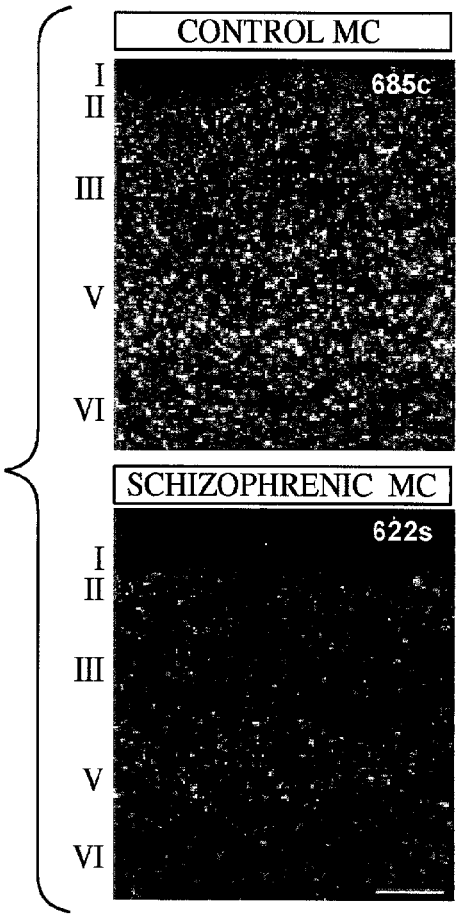
FIG. 4C shows high power photomicrographs of MC tissue sections from the same matched pair of schizophrenic and matched control subjects represented in FOG. 2A, viewed under darkfield illumination.
Figure 4B:
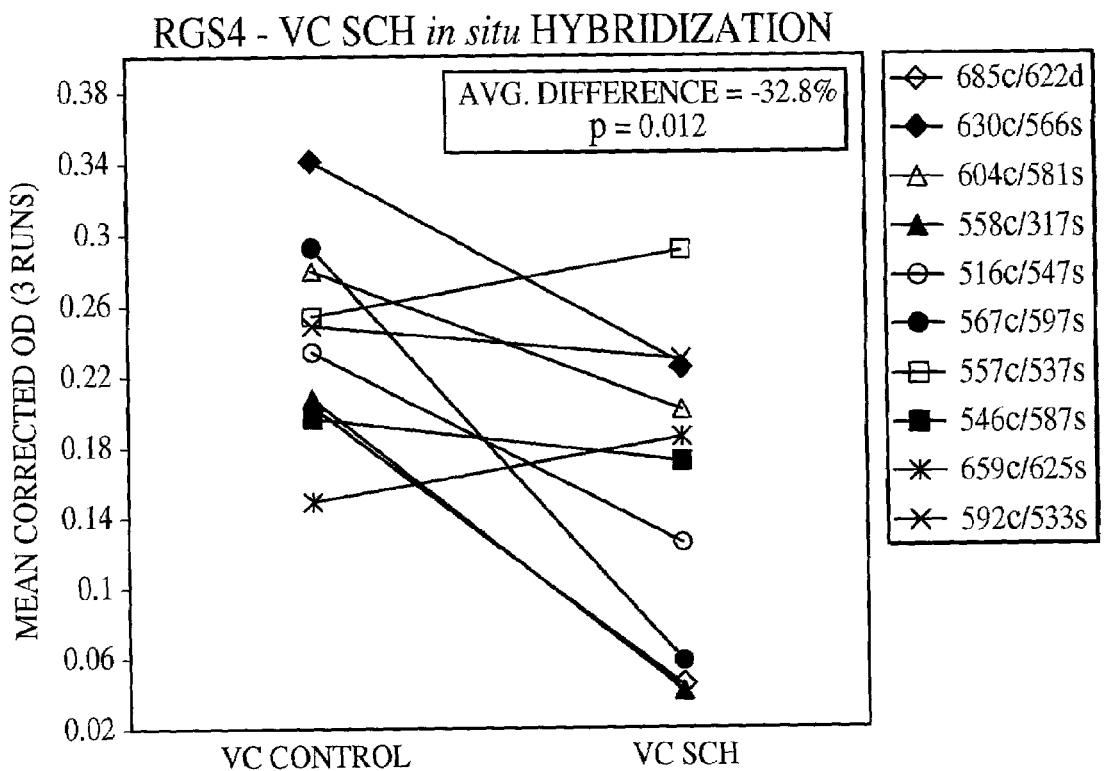
FIG. 4B shows a graph of 10 supragranular VC SCH pairwise comparisons, in which schizophrenic subjects showed a comparably significant RGS4 transcript reduction to the PFC comparisons.
Figure 4D:
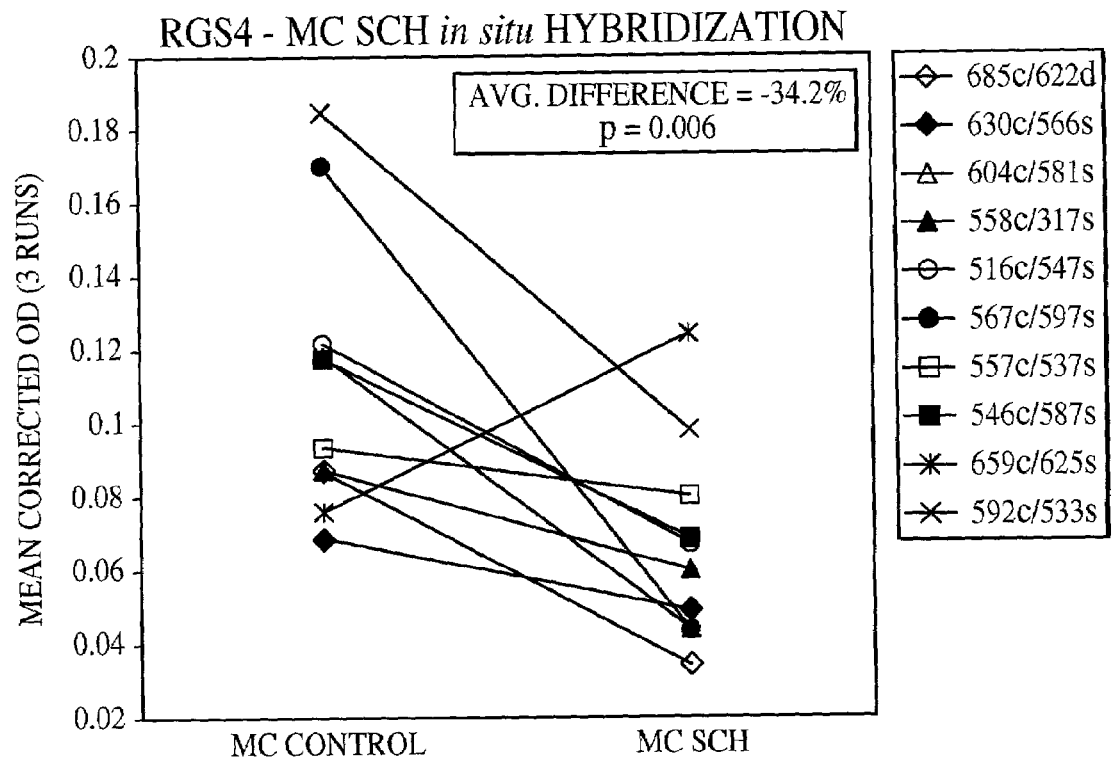
FIG. 4D shows a graph in which schizophrenic subjects across the same 10 subject pairs across the MC had comparably decreased RGS4 expression levels (mean=−34.2%, $F_{1,15}$=10.18; p=0.006) to VC and PFC.

Across the same ten pairwise comparisons that were examined in the PFC hybridizations, combined RGS4 expression in supragranular and infragranular layers of VC was decreased by 32.8% ($F_{1,15}$=8.24; p=0.012) as shown in FIG. 4B.

In MC, RGS4 expression was concentrated over the cell-rich layers I–III and V–VI of both control and schizophrenic subjects, as shown in FIG. 4C. High power photomicrographs of MC tissue sections from the same matched pair of schizophrenic and control subject are represented in FIG. 2A and FIG. 4A, viewed under darkfield illumination. Roman numbers denote cortical layers, scale bar=400 µm. Because of the attenuated layer IV in motor cortex, the RGS4 labeling is almost uniform across all layers.

Similar to the RGS4 transcript decrease observed in supragranular VC, schizophrenic subjects across the same 10 subject pairs were analyzed in MC. The mean RGS4 expression in MC shown in FIG. 4D, measured across all the layers, was decreased by 34.2% across the 10 schizophrenic subjects ($F_{1,15}$=10.18; p=0.006)

Figure 5:
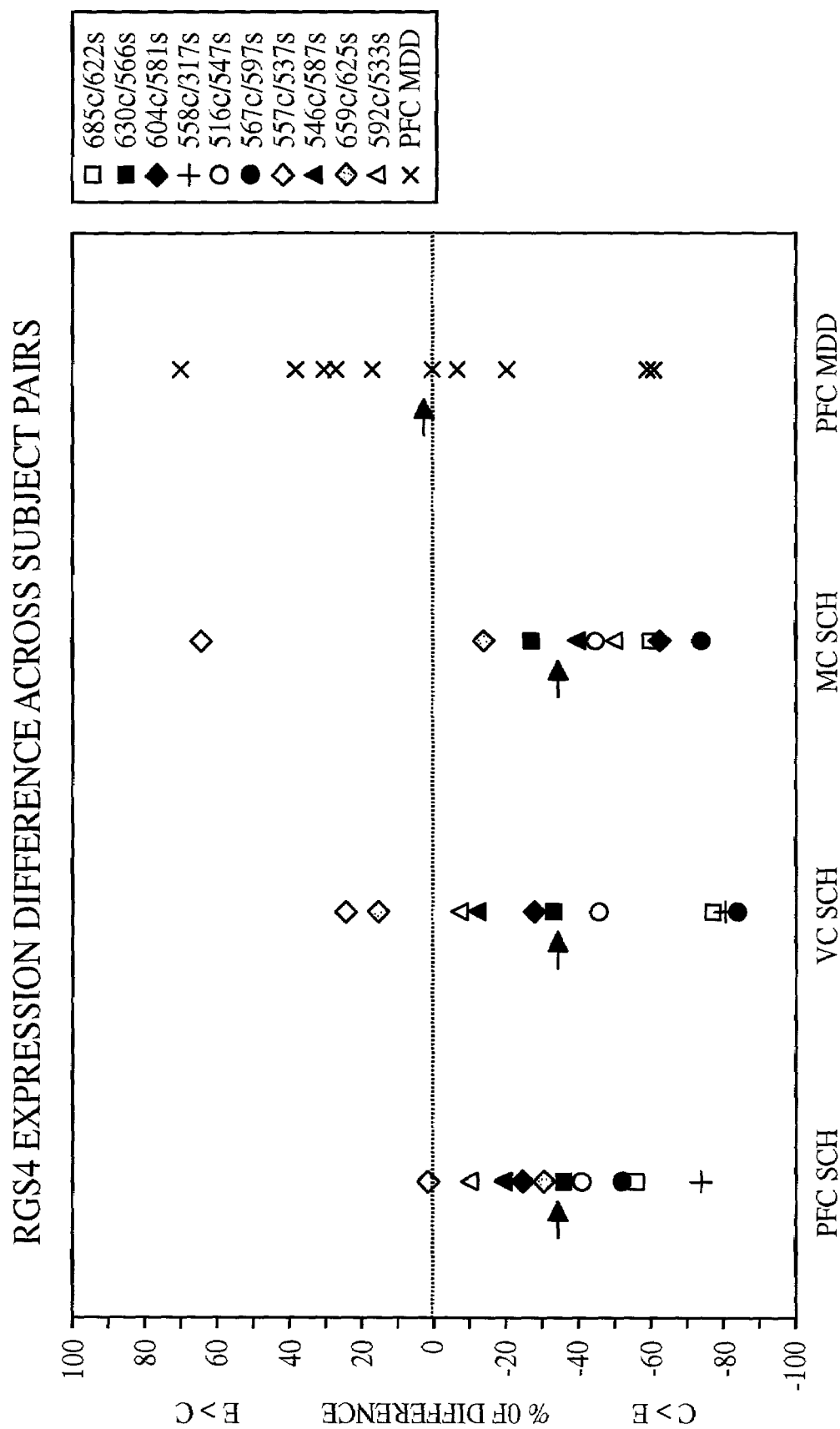
FIG. 5 shows a scatter plot of relative RGS4 expression changes across the experimental groups.

In the PFC, VC, and MC of subjects with schizophrenia, RGS4 expression was consistently decreased compared to the PFC of subjects with the diagnosis of MDD, as shown in the schematic of FIG. 5. In contrast, factor analysis of the pairwise differences in RGS4 gene expression across 3 different cortical areas for all 9 common schizophrenic and control subject pairs revealed that over 84% of the total variance in expression was accounted for by diagnosis (variance proportion=0.848, eigenvalue=2.544, p=0.001. The X-axis represents experimental groups, the Y-axis reports percent RGS4 expression change in PFC, VC, MC, in schizophrenic subjects (SCH) and PFC of subjects with MDD viewed by in situ hybridization. Each symbol represents percent of change between a single pairwise comparison; same symbols represent the same subject pairs. Arrows represent mean expression difference for each group. The same schizophrenic subjects showed a comparable and highly correlated decrease in RGS4 expression across all three cortical regions (PFC-VC: r=0.88, p=0.0003; PFC-MC: r=0.69, p=0.0384; VC-MC: r=0.76, p=0.0144). In contrast, subjects with MDD reported variable RGS4 expression changes when compared to their matched controls.

The combined data indicate that RGS4 transcript changes are a result of the pathophysiological changes related to schizophrenia and not due to confounds. Furthermore, the RGS4 expression decrease appears to be specific and unique to schizophrenia, and not a hallmark of the major depressive disorder.

RGS4 labeling in the white matter was comparable to background labeling across all brain regions, suggesting that RGS4 is primarily expressed in neuronal cells. The labeling was abundant in the majority of interneurons and projection neurons. However, in some pyramidal cells and interneurons RGS4 labeling could not be detected. RGS4 labeling was heavy in all cortical layers, except layer IV, where RGS4 expression was both sparse and light. This overall pattern of labeling was comparable across all three cortical regions (PFC, VC, MC). As the granular layer IV is the widest in the primary visual cortex, in this region RGS4 labeling was prominent in supragranular and infragranular layers, separated by a wide zone of mostly unlabeled granular cells. The overall distribution pattern of the RGS4 message does not mimic the known expression patterns of neurotransmitter systems, suggesting that RGS4 regulates many functionally distinct neuronal populations.

Together, the microarray and in situ hybridization methods suggest decreased RGS4 expression is a consistent characteristic of schizophrenic subjects. Several causes of the reduced RGS4 expression may be offered, including adaptive and genetic changes in schizophrenic patients. It was hypothesized that reduction in RGS4 expression was generated by alterations in the RGS4 gene. In addition, it was contemplated that variations in the DNA upstream and downstream from the coding region of the RGS4 gene may also impact the expression of the RGS4 transcript. These possibilities were investigated by searching for SNPs in the RGS4 gene.

The specificity of the reduced expression of RGS4 message for schizophrenic patients was confirmed in a series of control experiments. The same reduced level of RGS4 message was not observed in patients suffering from major depressive disorder. In addition, prolonged treatment of non-human primates with the anti-psychotic haloperidol did not result in decreased levels of RGS message in the cerebral cortex. This result indicates that chronic exposure to anti-psychotic drugs are unlikely to be responsible for the depressed levels of RGS4 message observed in schizophrenic patients.

Genotyping Results 34 single nucleotide polymorphisms (SNPs) were identified after re-sequencing all exons, introns and flanking 5' and 3' UTRs of the RGS4 coding region (FIG. 6). Thirteen SNPs were chosen for analysis using the TDT. SNPs are explicitly defined in Table 1. When the SNPs were tested individually, significantly increased transmission at SNP4 was observed in the Pittsburgh sample. 'Moving window' haplotype analyses using two to four contiguous SNPs, revealed significant association for several haplotypes; all but one included SNPs 1, 4, 7, or 18 (Table 2). A global test of association for haplotypes encompassing these SNPs was significant (TRANSMIT software, $\chi^2$=16.6, 8 df, p=0.035). There were 39 cases with schizoaffective disorder in the sample; these trends remained significant when the sample was restricted to individuals with schizophrenia ($\chi^2$=13.0, 6 df, p=0.043).

TDT analysis was conducted next in the ethnically diverse NIMH sample using the same set of SNPs. Significant transmission distortion was observed individually at SNPs 1, 4 and 18 (Table 2). Exclusion of African-American families from the sample also

TABLE 1

| SNIP # | Location of the SNP within the SEQ | Nucleotide identity in SEQ ID NO:3 | Observed Nucleotide variation |
|---|---|---|---|
| 27,859 | 199 {SEQ ID NO:4} | T | C |
| 34,653 | 153 {SEQ ID NO:5} | C | T |
| 90,387 | 87 {SEQ ID NO:6} | G | A |
| SNP1 | 4121 {SEQ ID NO:3} | C | T |
| SNP2 | 4123 {SEQ ID NO:3} | T | A |
| SNP3 | 4368 {SEQ ID NO:3} | A | C |
| SNP4 | 4621 {SEQ ID NO:3} | A | C |
| SNP5 | 4790 {SEQ ID NO:3} | C | T |
| SNP6 | 4816 {SEQ ID NO:3} | G | T |
| SNP7 | 4970 {SEQ ID NO:3} | C | T |
| SNP8 | 5055 {SEQ ID NO:3} | C | G |
| SNP9 | 5295 {SEQ ID NO:3} | G | A |
| SNP10 | 5695 {SEQ ID NO:3} | G | A |
| SNP11 | 7375 {SEQ ID NO:3} | G | T |
| SNP12 | 7759 {SEQ ID NO:3} | G | A |
| SNP13 | 8596 {SEQ ID NO:3} | G | A |
| SNP14 | 9603–9609 {SEQ ID NO:3} | AGTTTGG | 7 bases Absent |
| SNP15 | 9892 {SEQ ID NO:3} | C | A |
| SNP16 | 9963 {SEQ ID NO:3} | C | A |
| SNP17 | 10132 {SEQ ID NO:3} | G | A |
| SNP18 | 11056 {SEQ ID NO:3} | T | C |
| SNP19 | 11091 {SEQ ID NO:3} | C | T |
| SNP20 | 11106 {SEQ ID NO:3} | C | A |
| SNP21 | 11774 {SEQ ID NO:3} | G | T |
| SNP22 | 12143 {SEQ ID NO:3} | G | A |
| SNP23 | 12145 {SEQ ID NO:3} | G | T |
| SNP24 | 14367 {SEQ ID NO:3} | A | G |
| SNP25 | 17028 {SEQ ID NO:3} | A | Base absent |
| SNP26 | 17630 {SEQ ID NO:3} | G | T |
| 118740 | 120 {SEQ ID NO:7} | C | G |
| 130121 | 221 {SEQ ID NO:8} | G | C |

Location of single nucleotide polymorphisms relevant to the present invention. The location of the SNIP within the sequence is listed as is the variation observed in the collected samples. SNP 14 is the absence of the listed 7 bases at the indicated location.

revealed significant results for these SNPs (p=0.023, 0.011 and 0.033 respectively). However, the transmitted alleles differed from the Pittsburgh sample. Moving window haplotype analyses revealed preferential transmission for more extensive chromosomal segments than the Pittsburgh sample. Like the Pittsburgh sample, all but one of haplotypes with significant increased transmission included SNPs 1, 4, 7 or 18. A global test for association was also significant for haplotypes encompassing these SNPs (TRANSMIT analysis; $\chi^2$=18.8, p=0.016, 8 df).

If the significant TDT results were due to linkage, it was reasoned that the affected sibships in the NIMH sample should yield evidence for increased haplotype sharing. For 30 available affected sib-pairs, the proportion of 0, 1, or 2 haplotypes identical by descent (IBD) were elevated over expectations of 0.25, 0.50, 0.25; namely 0.11, 0.44, 0.45 respectively (for SNPs 1, 4, 7 and 18 analyzed in conjunction with 5 flanking short tandem repeat polymorphisms genotyped previously). Increased IBD sharing was also observed when these sets of SNPs or STRPs were analyzed separately.

Association at the population level was assessed by comparing Caucasian cases from each sample separately with two independent groups of Caucasian community-based controls. Since SNPs 1, 4, 7 and 18 appeared to be critical for transmission distortion in both samples, genotypes and allele frequencies for these SNPs were analyzed. Haplotypes frequencies were estimated using an expectation-maximization algorithm (EM), paying particular attention to haplotypes VI and XI, the haplotypes with excess transmission in the NIMH and Pittsburgh samples, respectively (Table 3). SNP 14 was informative only among African-Americans and so was analyzed separately using 70 African-American cases and 93 control individuals from Pittsburgh. Significant case-control differences were not noted for any of the comparisons. The failure to detect association may reflect superior power for the TDT in the context of population sub-structure.

TABLE 2

Haplotype based comparisons among cases and unrelated controls. The Caucasian cases from Pittsburgh (n = 93) and NIMH (n = 25) were compared separately with unscreened Caucasian controls from Pittsburgh (n = 76). Bonferoni corrections have been applied for the Pittsburgh case-control comparisons, but not for comparisons involving the NIMH cases. An omnibus test based on likelihood ratios was used to estimate overall differences in haplotype frequencies (Fallin et al., Gen. Res. 11, 143–51, 2001) and was significant for both comparisons ($\chi^2$ = 88.7, p < 0.0001 and $\chi^2$ = 30.1, p < 0.0003 respectively for Pittsburgh and NIMH cases). Similar significant differences based on 3 SNP haplotypes were present, but are not shown. For each SNP, 'o' represents allele 1 and '•' represents allele 2. OR—Odds ratio; NS—Not significant.

| No. | Haplotype SNP 1—4—7—18 | Neonatal Controls | Adult controls | Pittsburgh Cases | NIMH Cases |
|---|---|---|---|---|---|
| I    | o—o—o—o | 0.096 | 0.066 | 0.078 | 0.067 |
| II   | •—o—o—o | 0.004 | 0.021 | 0.022 | 0.083 |
| III  | o—•—o—o | 0.006 | 0.006 | 0.000 | 0.000 |
| IV   | •—•—o—o | 0.000 | 0.000 | 0.000 | 0.000 |
| V    | o—o—•—o | 0.000 | 0.000 | 0.006 | 0.000 |
| VI   | •—o—•—o | 0.806 | 0.842 | 0.874 | 0.692 |
| VII  | o—•—•—o | 0.000 | 0.006 | 0.000 | 0.000 |
| VIII | •—•—•—o | 0.000 | 0.000 | 0.006 | 0.000 |
| IX   | o—o—o—• | 0.000 | 0.004 | 0.000 | 0.017 |
| X    | •—o—o—• | 0.000 | 0.006 | 0.000 | 0.000 |
| XI   | o—•—•—• | 0.092 | 0.025 | 0.004 | 0.117 |
| XII  | •—•—o—• | 0.008 | 0.013 | 0.000 | 0.000 |
| XIII | o—o—•—• | 0.000 | 0.000 | 0.000 | 0.000 |
| XIV  | •—o—•—• | 0.053 | 0.013 | 0.017 | 0.025 |
| XV   | o—•—•—• | 0.006 | 0.000 | 0.000 | 0.000 |
| XVI  | •—•—•—• | 0.000 | 0.000 | 0.000 | 0.000 |

TABLE 3

Pair-wise linkage disequlibrium between SNPs at RGS4. Population based control individuals (n = 76) were used to estimate linkage disequilibrium. The figures above the diagonal represent D' and estimates for statistical significance (p values) are below the diagonal.

| SNP | 27859 | 90387 | snp1 | snp4 | snp7 | snp18 | snp23 | 118740 | 130121 |
|---|---|---|---|---|---|---|---|---|---|
| 27859  |        | 0.096  | 0.064  | 0.076  | 0.287  | 0.009  | 0.000 | 0.000 | 0.000 |
| 90387  | 0.132  |        | 0.000  | 0.000  | 0.000  | 0.000  | 0.000 | 0.001 | 0.627 |
| snp1   | −0.123 | −0.501 |        | 0.000  | 0.000  | 0.000  | 0.000 | 0.450 | 0.477 |
| snp4   | 0.101  | −0.501 | −1.000 |        | 0.000  | 0.000  | 0.000 | 0.128 | 0.515 |
| snp7   | −0.075 | 0.783  | 0.970  | −0.961 |        | 0.000  | 0.000 | 0.012 | 0.068 |
| snp18  | 0.177  | 0.377  | −0.677 | 0.989  | −0.961 |        | 0.000 | 0.000 | 0.041 |
| snp23  | 0.527  | −0.302 | −1.000 | 1.000  | −0.847 | 0.674  |       | 0.499 | 0.002 |
| 118740 | 0.385  | 0.163  | 0.048  | −0.083 | 0.172  | −0.233 | 0.042 |       | 0.000 |
| 130121 | −0.505 | 0.049  | −0.059 | 0.046  | −0.163 | 0.174  | −0.154 | −0.956 |     |

TABLE 4

SNPs and Haplotypes at RGS4 with increased transmission distortion. TDT analysis of case-parent trios included 93 families from Pittsburgh and 39 families from the NIMH cohort. Only statistically significant increased transmissions are shown. The shaded haplotypes correspond to haplotypes VII and X, respectively from Table 2. T/NT-Transmitted/not transmitted; o-Allele 1, ●-Allele 2 at each SNP; /-Allele not specified at this locus; *p < 0.05, p < 0.01, *p < 0.005

| Pittsburgh | | | NIMH | | |
|---|---|---|---|---|---|
| SNP | Transmitted allele | T/NT | SNP | Transmitted allele | T/NT |
| SNP 1 | o | 53/35 (0.055) | SNP 1 | ● | 30/13 (0.01) |
| SNP 4 | ● | 51/33 (<0.05) | SNP 4 | o | 22/6 (0.003) |
|  |  |  | SNP 18 | o | 24/8 (0.005) |
| Haplotypes (SNPs: 27859—90387—1—4—7—18—23—118740—130121—187688—208899—217761—322448) A B C D E F G H I J K L M | | | | | |
| /—/—/—/—/—/—/—/—/—/—/—/—/ | | | /—/—/—/—/—/—/—/—/—/—/—/—/ | | |
| /—●—o—●—/—/—/—/—/—/—/—/—/ |  | 34/18(0.03) | o—●—●—/—/—/—/—/—/—/—/—/—/ |  | 9/1(0.02) |
| /—●—o—●—o—/—/—/—/—/—/—/—/ |  | 33/14(0.006) | o—●—●—o—/—/—/—/—/—/—/—/—/ |  | 8/0(0.005) |
|  |  |  | /—●—●—o—/—/—/—/—/—/—/—/—/ |  | 11/3(0.04) |
| /—/—o—●—/—/—/—/—/—/—/—/—/ |  | 38/17(0.005) | /—/—●—o—/—/—/—/—/—/—/—/—/ |  | 23/3(0.0001) |
| /—/—o—●—o—/—/—/—/—/—/—/—/ |  | 37/13(0.0007) | /—/—●—o—●—/—/—/—/—/—/—/—/ |  | 19/3(0.001) |
| /—●—●—●—●—/—/—/—/—/—/—/—/ |  | 27/13(0.007) | /—●—●—●—●—/—/—/—/—/—/—/—/ |  | 23/3(0.001) |
| /—/—/—●—o—/—/—/—/—/—/—/—/ |  | 39/19(0.009) | /—/—/—o—●—/—/—/—/—/—/—/—/ |  | 20/7(0.02) |
| /—/—/—●—o—●—/—/—/—/—/—/—/ |  | 39/19(0.009) | /—/—/—o—●—o—/—/—/—/—/—/—/ |  | 20/7(0.02) |
| /—/—/—●—o—●—●—/—/—/—/—/—/ |  | 35/19(0.03) | /—/—/—o—●—o—●—/—/—/—/—/—/ |  | 11/3(0.04) |
| /—/—/—/—o—●—/—/—/—/—/—/—/ |  | 40/22(0.022) | /—/—/—/—●—o—/—/—/—/—/—/—/ |  | 20/7(0.02) |
|  |  |  | /—/—/—/—●—o—●—/—/—/—/—/—/ |  | 11/3(0.04) |
|  |  |  | /—/—/—/—/—o—●—/—/—/—/—/—/ |  | 20/6(0.006) |
|  |  |  | /—/—/—/—/—o—●—●—/—/—/—/—/ |  | 20/4(0.001) |
|  |  |  | /—o—●—/—/—/—/—/—/—/—/—/—/ |  | 11/3(0.04) |
|  |  |  | /—o—●—o—/—/—/—/—/—/—/—/—/ |  | 11/3(0.04) |
|  |  |  | /—/—●—o—o—/—/—/—/—/—/—/—/ |  | 4/0(0.05) |
|  |  |  | /—/—●—o—o—o—/—/—/—/—/—/—/ |  | 4/0(0.05) |
|  |  |  | /—/—/—o—o—●—/—/—/—/—/—/—/ |  | 7/1(0.04) |
| /—/—/—/—/—/—/—o—●—o—o—/—/ |  | 6/0(0.01) | /—/—/—/—/—/—/—/—o—●—o—● |  | 5/0(0.03) |

The demonstration of the association between these SNPs and schizophrenia offers a large number of applications in the diagnostic and therapeutic fields. Thus, embodiments of the present invention offer the possibility of diagnosing schizophrenia by means of a biological test and no longer exclusively by means of clinical evaluations. Embodiments of the present invention can also be applied to diagnosing pathologies of the schizophrenia spectrum, such as, in particular, schizotypy, schizoid individuals, etc. Embodiments of the present invention make it possible to refine the criteria for diagnosing these pathologies, which is currently entirely established clinically. Furthermore, embodiments of the invention also makes it possible to demonstrate susceptibility to schizophrenia by means of identifying a genetic vulnerability in the families of patients who posses the identified SNPs in the RGS4 coding region and flanking regions. Once individuals have been identified as being susceptible to schizophrenia, the utility of prophylactic treatment may be investigated.

The DNA sample to be tested can be obtained from cells that have been withdrawn from the patient. These cells are preferably blood cells (e.g. mononucleated cells), that are easily obtained by the simple withdrawal of blood from the patient. Other cell types, such as fibroblasts, epithelial cells, keratinocytes, etc., may also be employed. The DNA may then extracted from the cells and used to detect the presence of SNPs in the RGS4 coding region and flanking regions.

Most preferably, the DNA extract is initially subjected to one or more amplification reactions in order to obtain a substantial quantity of material corresponding to the region carrying the RGS4 coding region and flanking regions. The amplification can be achieved by any technique known to the skilled person, and in particular by means of the so-called PCR technique as described above. To this end, embodiments of the present invention also relate to specific primers which make it possible to amplify DNA fragments that are of small size and which carry the RGS4 gene, flanking regions thereof, or portions thereof generated from SEQ ID NOS. 3, 4, 5, 6, 7, or 8. Portion of a polynucleotide sequence is specifically intended to refer to any section of SEQ ID NOS. 3, 4, 5, 6, 7, or 8 that can be used in the practice of this invention, such as use as a primer to identify the presence of SEQ ID NOS. 3, 4, 5, 6, 7, or 8 or variations thereof in a patient or a section of SEQ ID NOS. 3, 4, 5, 6, 7, or 8 that can be used to amplify the entire sequence. The phrase contiguous portion is meant to refer to a series of bases that are adjacent to one another within a polynucleotide sequence. In the context of the present invention, the word gene is intended to mean the protein coding region, the proximal 5' and 3' untranslated regions, as well as any distal and proximal regulatory domains. The phrase gene-coding region is meant to refer to the stretch of DNA that begins at the transcription initiation site and includes all exionic and intrionic sequences that encode a protein.

Embodiments of the present invention may also involve isolating DNA sequences and ligating the isolated sequence into a replicative cloning vector which comprises the isolated DNA of the RGS4 gene, based upon or derived from the cDNA of SEQ ID NOS. 3, 4, 5, 6, 7, or 8 and a replicon operative in a host cell. Additional embodiments include an expression system which comprises isolating DNA of the RGS4 gene, based upon complimentarity to SEQ ID NOS. 3, 4, 5, 6, 7, or 8 and operably linking this DNA to suitable control sequences. Recombinant host cells can be transformed with any of these replicative cloning vectors and may be used to overproduce the RGS4 protein.

Embodiments of the present invention also include kits that will facilitate the diagnosis of schizophrenia through the amplification of segments of the 1q21-22 locus. Several methods providing for this amplification are described including: at least a pair of single-stranded DNA primers wherein use of said primers in a polymerase chain reaction results in amplification of a portion of the RGS4 gene fragment, wherein the sequence of said primers is derived from the regions of the cDNA defined by or complementary to SEQ ID NOS: 1, 3, 4, 5, 6, 7, or 8. Similarly, embodiments of the invention also provide for a pair of single-stranded DNA primers wherein use of said primers in a polymerase chain reaction results in amplification of an RGS4 gene fragment, wherein the sequence of said primers is based on the exon regions of chromosomal DNA derived from SEQ ID NOS:1 or 3.

Various nucleic acid probes and primers specific for RGS4 (derived from or complementary to SEQ ID NOS. 3, 4, 5, 6, 7, or 8) may also be useful in diagnostic and therapeutic techniques and are included within the present invention. Among these are a nucleic acid probe complementary to portions or the entirety of human RGS4 gene as well as a nucleic acid probe complementary to human altered RGS4 gene sequences wherein said nucleic acid probe hybridizes to a variant of the RGS4 gene under hybridization conditions which prevent hybridizing of said nucleic acid probe to a wild-type RGS4 gene. Probes that are complementary to portions or the entirety of the RGS4 coding region and flanking regions that contain SNPs may also be used in these diagnostic tests. Any primer which makes it possible to amplify a fragment of the RGS4 coding region or flanking regions also forms part of the present invention. The primers that are used within the context of the invention can be synthesized by any technique known to the skilled person. The primers can also be labeled by any technique known to the skilled person.

The invention may also be practiced through detection of SNPs in the RGS4 coding region or flanking regions by a variety of techniques. The techniques which may preferably be employed are DNA sequencing and gel separation.

Any sequencing method known to the skilled person may be employed. In particular, it is advantageous to use an automated DNA sequencer. The sequencing is preferably carried out on double-stranded templates by means of the chain-termination method using fluorescent primers. An appropriate kit for this purpose is the Taq Dye Primer sequencing kit from Applied Biosystem (Applied Biosystem, Foster City, Calif.). Sequencing the SNPs in the RGS4 coding region and the flanking regions makes it possible to identify directly the SNPs that are present in the patient.

An additional preferred technique for demonstrating the SNPs in the RGS4 coding region and flanking regions is that of separation on a gel. This technique is based on the migration, under denaturing conditions, of the denatured DNA fragments in a polyacrylamide gel. The bands of DNA can be visualized by any technique known to the skilled person, with the technique being based, such as by using labeled probes that are complementary to the entirety or portions of the RGS4 coding region and flanking regions. Alternatively, the bands may be visualized by using ethidium bromide or else by means of hybridization with a radiolabeled probe.

In addition, measuring the expression of RGS4 message in peripheral tissue allows the diagnosis and determination of the susceptibility to schizophrenia in humans. As a matter of convenience, the reagents employed in the present invention can be provided in a kit packaged in combination with predetermined amounts of reagents for use in determining and/or quantifying the level of RGS4 expression. For example, a kit can comprise in packaged combination with other reagents any or all of the following components: appropriate detectors, buffers, deoxynucleotide triphosphates, ions provided by $MgCl_2$ or $MnCl_2$, and polymerase(s). The diagnostic kits of the invention may further comprise a positive control and/or a negative control as well as instructions for quantitating RGS4 expression.

Additionally, an embodiment of the present invention relates to ascertaining levels of the RGS4 protein. The level of RGS4 protein can be detected by analyzing binding of a sample from a subject with an antibody capable of binding to RGS4. An embodiment of this detection method utilizes an immunoassay. The sample from a subject may preferably be a biopsy of skeletal muscle, though any tissue accessible to biopsy may be used.

In addition to providing generally useful diagnostic kits and methods, embodiments of the present invention may provide a method for augmenting traditional treatments by supplying the RGS4 protein to a subject and/or augmenting the subject's medication, such as antipsychotic drugs, and providing an improved therapeutic outcome.

Further embodiments of the present invention may relate to the construction of an animal model of schizophrenia. Transgenic mice technology involves the introduction of new or altered genetic material into the mouse germ line by microinjection, retroviral infection or embryonic stem cell transfer. This results in lineages that carry the new integrated genetic material. Insertional mutagenesis occurs when integration of the microinjected genetic material into the host genome alters an endogenous gene resulting in a mutation. Methods of transferring genes into the germline, the expression of natural and hybrid genes and phenotypic changes that have occurred in transgenic mice are described by Palmiter and Brinster in Ann. Rev. Genet. 20 (1986) 465–499. Methods of foreign gene insertion, applications to foreign gene expression, and the use of transgenic mice to study immunological processes, neoplastic disease and other proliferative disorders are described by Gordon in Intl. Rev. Cytol. 115, 1989, 171–299 both of which are hereby incorporated by reference. A further example of genetic 'knock-in' technology may be found in Nebert, et al., Ann. N.Y. Acad. Sci. 919, 2000, 148–170 which is hereby incorporated by reference. The insertion of SEQ ID NO:3 containing some or all of the described SNPs into a mouse germ line may be expected to result in adult mice that may be used as an experimental model of schizophrenia. The insertion of SEQ ID NO:3 containing one or more of the variations listed in Table 1 with standard on:off regulatory domains will allow for the creation of mice deficient in RGS4 expression at specified times, and may be used as an experimental model of schizophrenia.

Having now fully described embodiments of the present invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention.

What is claimed is:

1. An isolated and substantially purified DNA sequence comprising SEQ ID NO:3, wherein SEQ ID NO:3 includes at least one variation selected from the group consisting of:
   a T at nucleotide base number 4121 of SEQ ID NO:3;
   a C at nucleotide base number 4621 of SEQ ID NO:3;
   a T at nucleotide base number 4970 of SEQ ID NO:3;
   a C at nucleotide base number 11056 of SEQ ID NO:3; and
   a T at nucleotide base number 12145 of SEQ ID NO:3.

2. A hybridization probe comprising the DNA sequence of claim 1 and a detectable label.

3. An isolated host cell comprising a vector, wherein said vector further comprises SEQ ID NO: 3.

4. The isolated host cell of claim 3, wherein SEQ ID NO:3 includes one or more of the variations selected from the group consisting of:
   a T at nucleotide base number 4121 of SEQ ID NO:3;
   a C at nucleotide base number 4621 of SEQ ID NO:3;
   a T at nucleotide base number 4970 of SEQ ID NO:3;
   a C at nucleotide base number 11056 of SEQ ID NO:3; and
   a T at nucleotide base number 12145 of SEQ ID NO:3.

5. A DNA sequence that is one hundred percent complementary to the DNA sequence of claim 1.

* * * * *

UNITED STATES PATENT AND TRADEMARK OFFICE
CERTIFICATE OF CORRECTION

PATENT NO. : 7,166,462 B2  Page 1 of 1
APPLICATION NO. : 09/939209
DATED : January 23, 2007
INVENTOR(S) : Levitt et al.

It is certified that error appears in the above-identified patent and that said Letters Patent is hereby corrected as shown below:

Title page, item [73], Assignee:

"Vanderbult University" should be --Vanderbilt University--

Signed and Sealed this

Nineteenth Day of June, 2007

JON W. DUDAS
*Director of the United States Patent and Trademark Office*

SEQUENCE LISTING

<160> NUMBER OF SEQ ID NOS: 8

<210> SEQ ID NO 1
<211> LENGTH: 2934
<212> TYPE: DNA
<213> ORGANISM: Homo sapiens

<400> SEQUENCE: 1

```
gtacgctcaa agccgaagcc acagctcctc ctgccgcatt tctttcctgc ttgcgaattc      60
caagctgtta aataagatgt gcaaagggct tgcaggtctg ccggcttctt gcttgaggag     120
tgcaaaagat atgaaacatc ggctaggttt cctgctgcaa aaatctgatt cctgtgaaca     180
caattcttcc cacaacaaga aggacaaagt ggttatttgc cagagagtga gccaagagga     240
agtcaagaaa tgggctgaat cactggaaaa cctgattagt catgaatgtg ggctggcagc     300
tttcaaagct ttcttgaagt ctgaatatag tgaggagaat attgacttct ggatcagctg     360
tgaagagtac aagaaaatca aatcaccatc taaactaagt cccaaggcca aaaagatcta     420
taatgaattc atctcagtcc aggcaaccaa agaggtgaac ctggattctt gcaccaggga     480
agagacaagc cggaacatgc tagagcctac aataacctgc tttgatgagg cccagaagaa     540
gattttcaac ctgatggaga aggattccta ccgccgcttc ctcaagtctc gattctatct     600
tgatttggtc aacccgtcca gctgtggggc agaaaagcag aaaggagcca agagttcagc     660
agactgtgct tccctggtcc ctcagtgtgc ctaattctca cctgaaggca gagggatgaa     720
atgccaagac tctatgctct ggaaaacctg aggccaaata ttgatctgta ttaagctcca     780
gtgctttatc cacattgtag cctaatattc atgctgcctg ccatgtgtga gtcacttcta     840
cgcataaact agatatagct tttggtgttt gagtgttcat cagggtggga ccccattcca     900
gtccaatttt cctaagtttc tttgagggtt ccatgggagc aaatatctaa ataatggcct     960
ggtaggtctg gattttcaaa gattgttggc agtttcctcc tcccaacagt tttacctcgg    1020
gatggttggt tagtgcatgt cacatgacat ccacatgcac atgtattctg ttggccagca    1080
cgttctccag actctagatg tttagatgag gttgagctat gatatgtgct tgtgtgtatg    1140
tctatgtgta tatattatat atacattaga cacacatata cattatttct gtatatagat    1200
gtctgtgtat acatatgtat gtgtgagtgt atgtatacac acacacacac acacacacac    1260
acacttttgc aagagtgatg ggaaagaccc taggtgctca taactagagt atgtgtatgt    1320
acttacatgg gtgttttgat ctctgttctt tcatactaca tttgaacagg gcaaaatgaa    1380
ctaactgcca tgtaggctaa gaaagaaatg ctaacctgtg gaaagttggt tttgtaaaat    1440
```

-continued

```
tccatggatc ttgctggaga agcatccaag gaacttcatg cttgatttga ccactgacag    1500
cctccacctt gagcactatt ctaaggagca ataccttag ctcccttgag ctggttttct     1560
ctgatggcac ttttgagctc ctaagctgcc agccttccct tcttttcctg ggtgctcagg    1620
gcatgcttat tagcagctgg gttggtatgg agttggcaga caggatgttc aacttaatga    1680
agaaatacag ctaaggcctt gccagcaaca cctgccgtaa gttactggct gagtgagggc    1740
atagaagtta aaggttactg ttttatcct ctatccttt ttcctttcct gatcaaggtg      1800
ctcttctcat ttttcctga gaaccttagc catcagatga ggctccttag tttattgtgg    1860
ttggttgttt tttctttata atggctctgg gctatatgcc tatatttata aaccagcagc   1920 agggaaaga ttatatttta taagagggaa caaattttca caatttgaaa gcccacata     1980 agttttctct tttaaggtag aatcttgtta atttcattcc aaacatcggg gctaacagag   2040
actggaggca tttctttta ggctctgaga ctaaatgaga ggaaaagaaa agaaaaaaaa    2100
aatgattgtc taaccaattg tgagaattac tgtttgaaac ttttcaaggc acattgaaat   2160
acttgaaaac ttctcattta tgttatttat gatgttattt tgtacgtgtt attattatta   2220
tattgtttta taaatggagg tacaggatat cacctgaatt attaatgaat gcccaggaag   2280
taattttctt ctcattcttc taaaactact gcctttcaaa gtgcacacac acgcgtccac   2340
atacactgca ttcgttgctc cagtataaat tacatgcatg agcacctttc tggcttttaa   2400
gccaatataa tgggctgcaa aatgaagaca ccagagtgta tgcatacaaa tctcactgta   2460
ttaaagatgc aggttttcta attgtaccct tcttgtctct ctggcaatct tgcccttaat   2520
atccctggag ttcctcatca gtgtcatttt ctgttataca cagttccaca attttgtctc   2580
tagttgactt caaatgtgta actttattgg tcttgcccta ttataattgt catgactttc   2640
agattgtatc tgaactcaca gactgctgtc ttactaatag gtctggaagg tcacgctgaa   2700
tgagaagtaa attattttat gtaatacatt tttgagtgtg ttttcagtt gtatttccct    2760 gttatttcat cactatttcc aatggtgagc ttgcctgctc atgctccctg gacagaatac   2820
tccttccttt tgcatgcctg tttctatcat gtgcttgata ggcctcaaag ctaatgcttc   2880
cagtgaaaca cacgcatctt aataataagg gtaaataaac gctccatatg aaac          2934
```

<210> SEQ ID NO 2
<211> LENGTH: 205
<212> TYPE: PRT
<213> ORGANISM: Homo sapiens

<400> SEQUENCE: 2

```
Met Cys Lys Gly Leu Ala Gly Leu Pro Ala Ser Cys Leu Arg Ser Ala
1               5                   10                  15

Lys Asp Met Lys His Arg Leu Gly Phe Leu Leu Gln Lys Ser Asp Ser
            20                  25                  30

Cys Glu His Asn Ser Ser His Asn Lys Lys Asp Lys Val Val Ile Cys
        35                  40                  45

Gln Arg Val Ser Gln Glu Glu Val Lys Lys Trp Ala Glu Ser Leu Glu
    50                  55                  60

Asn Leu Ile Ser His Glu Cys Gly Leu Ala Ala Phe Lys Ala Phe Leu
65                  70                  75                  80

Lys Ser Glu Tyr Ser Glu Glu Asn Ile Asp Phe Trp Ile Ser Cys Glu
                85                  90                  95

Glu Tyr Lys Lys Ile Lys Ser Pro Ser Lys Leu Ser Pro Lys Ala Lys
            100                 105                 110
```

```
Lys Ile Tyr Asn Glu Phe Ile Ser Val Gln Ala Thr Lys Glu Val Asn
            115                 120                 125
Leu Asp Ser Cys Thr Arg Glu Glu Thr Ser Arg Asn Met Leu Glu Pro
        130                 135                 140
Thr Ile Thr Cys Phe Asp Glu Ala Gln Lys Lys Ile Phe Asn Leu Met
145                 150                 155                 160
Glu Lys Asp Ser Tyr Arg Arg Phe Leu Lys Ser Arg Phe Tyr Leu Asp
                165                 170                 175
Leu Val Asn Pro Ser Ser Cys Gly Ala Glu Lys Gln Lys Gly Ala Lys
            180                 185                 190
Ser Ser Ala Asp Cys Ala Ser Leu Val Pro Gln Cys Ala
            195                 200                 205

<210> SEQ ID NO 3
<211> LENGTH: 20300
<212> TYPE: DNA
<213> ORGANISM: Artificial Sequence
<220> FEATURE:
<221> NAME/KEY: misc_feature
<223> OTHER INFORMATION: A genomic sequence containing RGS4 nucleic
      acid sequence and sequences upstream and downstream
      to the RGS4 nucleic acid sequence

<400> SEQUENCE: 3
agttcaagac cagcctgagc aacatggtga accccatct ctactaaaaa tacaaaatta      60
gacaggcatg gtgatacacg cctgtaatcc cagctacttc ggaggccgag gcaggagaat   120
cacttgaacc tgctgggggt ggaggttgcg gggagcaaga tcatgccatt gcactccagc   180
ccaggcaaca agagcgaaat gtcatctcag aaaaaaaaaa aggcatttta tatatatata   240
tatatatata tacacacaca cacacatata tatacacaca tatatataca catatataca   300
tatatacaca tatatacaca tatatacaca catacatatg tacacatata tatacacata   360
tgtatacaca tatatacaca tatatacaca catatataca catatataca cacatatata   420
cacatatata cacatatata cacatataca catatataca catatataca tatatacaca   480
tatatataat atacacacat atatatacac atatatacac acatatatac acatatatac   540
acatatatat acacatatat acacatatat acatatatac acatatatat acatatatac   600
acatatatac atatatacac atatatacat atatacacac atatatacac atacatatac   660
acacacatag atatacatat atatacacat atatatacgt atatatatgt atatatatat   720
gctccagagt tcataagagg tagcagttga ttaccactgg ggatagagga aaagagagtt   780
tgacagcagt gtattgtgag aaggacattt caggttgatg gcaaatagta ggggaaatac   840
ataaatgtgt aataaaacct atctgtaagg tagttaagaa ggtaacacta tatatatata   900
tagtgaaagc agtgtaaacc taaaggatgg gccaaggatt taaatgttat agaagaatgg   960
ctaagatgcc aaagctcagt gtatgtggca gaggcatggt gtagggtgtg tccaggttca  1020
tatattgcat taagtgtgag aacaccctgg agtatgaacc aagaaaatgc aaaagccaga  1080
agtgatggag gaaatgagac acaataatga agatattgag aggagggtgt gggcctagag  1140
tgaagctttt cgtgccagta cttcttttga aggcccagtt ctcttctctc tcggggggctc  1200 cttcatctct catagagtcc acagcttta agggccaaca cttgaggtca gcctggctct  1260
ctcatttgag ctggatagaa cattttagag caccatctat tcttcaagag gaagtttaaa  1320
aataaaagaa ccttgaagag gaaaaaatgt agacattcaa tctaaccttt tcattttact  1380
agccaaagct aaatagaatg caggttacct gttttttcagc caggcaccat catttcctaa  1440
```

-continued

```
ttgttataaa atttattatt attgttgtta ttattattat ttgccataag aagtttccca    1500
tatccttta gtataacaaa aacacaattc acaagcatta taaaacccat ggtgtctaac    1560
tattaaaaaa attaagtgga acacacttgt cccagctact ggggaggctg aggagggagg    1620
atcacgtgat cccagggggt caaggttatg agagctatg attgtgccac tgcactccag    1680
cctgggtgac agggaaagac cctgtctcta aatttttt taaaaaaact aaactggttt    1740
tattacagag attctggaga cagctacaca taaaagggtg gtatgcctca tattagctac    1800
ccagggaggt ggaatgccaa cttaggtggt gtcaccacta ttaaaaatgc cccaaagcaa    1860
tcaaaactga gaacttcctg ggagcttagc attgtgcaaa agcagcacaa aacacttaaa    1920
caattcacag ttgtgttgga atgggaaggc ctggaaatat aaaccaaaga gtatattgtc    1980
taaattgata gagattacaa ttgcctgaaa gaaaaagttg acttttaact agaatgttca    2040
gagtaggttt acagaagaag ctcttaaact gggctccagt ggatttgtca atgctttgga    2100
agctggtggg gtgggagggt tggaggggggc ataaaaagtc atgttggtat gctctgctca    2160
agtctccatt ctgtttcctt ttcctctttt caatgtcatg tcccattatt tcattatggg    2220
cttccctta tccaggatca atatgccacc tcttggttgt cttttaccta cttctccacc    2280
tcactatgga atcgtccttg ggtagctcct gtgcttggga acctgcacgg gcactttct    2340
gatgtcttga ttccagcttt actcctaaaa cttaaatgct gaggggccaa caccatggca    2400
gtggtaggga tgggaatggg ggtcttgtaa cacactacat aaaactacg aaataaaacta    2460
catgaaactc aacatgtttg caagactcag ttcacatcca tgaggagctc atgcttctcc    2520
ctcctgctcc cctagcacac atgattatct ctatttggaa atgtttggca ttttggtga    2580
agtgaatggt tcaataactt tctccaccat cagaacaaaa gctctttaag gttagggatg    2640
ggatcataca cacttccctt gtccaagtcc ccatcaccc ttatctagac aattgctaca    2700
gtttcctaca cactcttcta acctcttgca gtctattttc ataaaacagc tagagaactt    2760
tgagatgtaa gtcaaaaaat agaacatgtc gctctttccc attgtttttg aaataaagtt    2820
caacccctt accagggtca acaaggccct gcaatgattt ggtcctgtta aaaattcttt    2880
agccttaact catgctgttc ttccttacac tcactgcatt ctagccattg aggtttctat    2940
gcatcaaact tttttggtc ccagcactgt gcacatcctt ctgggtagaa tgccccttga    3000
tttgtataat tagcacctcc ttcatcattt aggtcttagt ataactacta ccttcttaga    3060
gaagctctgc ttcttcatcc tataaaaaag taaaattcct taccctgtta ttttttaagt    3120
catccgtgtt tcattctgtt aaagttctta tcacaattta tcattatttt atttacagtc    3180
atgtgccaca taacaatgtt tcagtcaggg atagaacaca aatgtatctg gccccataat    3240
attataagct gagaaatttc tattaactag tgatatcgca gccatcataa gtgtaatgca    3300
ggacattacc ttttctatgt ttagatatgt tagatacaca aatatatttc attgtgttat    3360
aatttcctac agtattcagt acagtaacat gctgtacagg tttgtaaccct aggagtaata    3420
ggctatacca tacagcttag gtgtgtagta ggctataacc atctaggttt gtgtaagtac    3480
attctatgat attcccacaa tgatgaaatc acctaactac acatttctca gaatgtttca    3540
ctgttgtgaa gtgacccatg actatatttt cctatatact tgatatttt gtgcatctgc    3600
ccatgagaat gtagtgtaag atcaaaggat gcaagaatgg gttctatcca gtatagtacc    3660
cactacactg gtggatgtca atatgtattt gttagattaa tatctcaaga atgagcacct    3720
ttctcagaca cataaaagat gctcaatata aagtttgtt gaactgaacg ttattggcaa    3780
```

```
atgtaacatg atcggattta aagaggagcg aaacagaggt ctggctcaaa caccatactt    3840
ctagagtgca taagaggtag cagttgatta ccactggcga caggagaaaa aagagcttga    3900
ccgcagggta ctgtgaagac atttcaggtt gatggcacag aacagggaa atacataaat    3960 gtgtgggaat attcagtggt ctgggatgac tacatagtag aatataatga agaaaagagt    4020
ggaagggaaa gatgaaaagt tggaatgggg atgaattatg aaagtaccag aatgttatgc    4080
taaggaatct agattttaaa atgtgaggc aaattgaagt cctgggcacg ttacaaaact    4140
agaggtcata aagtttaccc taatttacca agatttccta gaggatctat aattggaatc    4200
cagatctgcc tctctgtaaa gttcaagcac tttccatgac accatactgt ttctttccac    4260
ctgcacaatg caaatgaact cttatgaaac tgctgtttct atcctgggct aaatgttgca    4320
gaaaaaagat ttaatctttg ggataaggct attttgggtt ttctcctact tcttgggaaa    4380
caaggttttc ttcccctggc taattaagtg tggtattgtt cttccaggga atcagtgat    4440 gcatcacctg ctgctatcaa atgtcaggt tggagttcct gatttattgc atgtgcccac    4500
aaagcttggt gcaaagaatt ggacacattt cccaaaagta agacatactg ggaagtccct    4560
gtttaccttc ctggtataca gcatcctcca gccccatatc tttgctttt agtcctaaaa    4620 atcaataact gaactctcat tgatgtctag gccattgtag taaacaataa agaaggaggg    4680
aggcttctga caactgagag gaaattgtca tctgaagtgg tgcaagcaca gcctgggct    4740 gagccttggc ctacatcctg cccaagtgga ggatcagtgc cccatttaac atctggtaga    4800
actaaagaac gcaacgcctg ccacaatgac ttattttccct gcatttgata ccgtcaatcc    4860
ttgagaaatg ttttcttttg ttctcctga gcaaaggttg gaaaaatttg aaatttacct    4920
agagaccaca catagttcac atcctgctgt gtggctgaat gtctgccccc cagtaggaaa    4980
cagttcttct aaagcctatt gtcaacaata ccttccagat gttagcattt acaatttaa    5040 ggaacttaaa atagccttca aacttttttgc cagtttctct gatatccaat ctattctttt    5100
actctgcctc ccaagctttc tttctagaat gctaacctga tcggcttaag tacttgaact    5160
acctcttctc ctccattaac tacagagtaa attctggtct tcagagtaac aagaaacacc    5220
ctttagttct cagcatattc gtgcaccttc atttatctct ccttctctct caaagctgca    5280
gtaggggtga aaacgtgtga tacattttct cttccatcat aagggtcgca accaaaactc    5340
ctatagtaaa agacaggtta ataagagcaa aacctaacaa atttatttaa tcaaagtttt    5400
acatgacatg ggagtcttca gaaatgaaga cccaaagacc caggggaaac tgtctgtttt    5460
ttttgctgag gttcgatgaa gaatggatag catgtagcca tgtagattag acaaaaggat    5520
atgatctagt ggtaaaggac tcagggggaa acacagcaag gcctgtctat tcagattctt    5580
cttgatctct ctctctctat gtatagcatt cttttcctcct gagtatgggg caggactctt    5640
cttcaatgag ggtcttcaag ggagaaggga gaaagtggcc ttttttagatt ttatggcttg    5700 cttcggggaa gaggagttct agtttctatg acccatcttg gggaagagga attctggttt    5760
ctgtgacttg ctttcatgaa gaaagaggag taagaggcag gagggcagga gatggtcaga    5820
aagagacttg gctgcttctg agggcttccg ctctccttta gttccaagta cttcttagca    5880
taccaaagca ctatactttg gcatatggtt ttctgagctc taacactgca atcatgctaa    5940
actcctctat gaccttcaaa cattccactt gcttttattc tttatggttg tgatggcata    6000
gaggtcaata gcaaagaccc tggagtccca ctgtctgagc tggcataaca ttactaccac    6060
ttaatcaatg tgtaagctca ggtaagtact taagtcctct atgcttcatc tgtaaaatga    6120
gaatcattga agaacattct ctcaggatgg atcatgagga ataagtgaat taactggcat    6180
```

```
atagtgctta aaccagtgcc ttgctcagtt agtgacagat aaaatcatct gttattactg    6240
tgcccactat tgtgatgctc ttctcttctt tgtacaacga ctacatctct atttatcatt    6300
ttagggtctc cttgtgaaaa accactccag attcaaaaga ttgagtttaa tctctatcct    6360
ctgtgctttc ctggagtttt gtaaagtaaa tcttcacttg acatcatgga taggttcttg    6420
gaaactacaa cttcaagtga aaggacataa ctaaaccaat ttttttctca tcaacgttat    6480
aatgaaatgg cattgatgaa atgatggcat tcaaggacct gctgtaccct gtttcactta    6540
aagtcactgt ttccaataat ctattgatga cattgaggac ttactatata ataataaata    6600
tatatataat cgacgaaaca ggaatcaaac tgctaactct gctaactggt ctccctgctt    6660
ccacactctg cccactcatc tcagtctttc tttcacaaga gtcagaatga tcagatgaga    6720
cccctcctct gcttctgttt cttccatgga tttccactgc actctgataa agtccagcct    6780
cttgaccaca gcctacaaat ccttgcacga tctatcgttt acttttccat ctccttttat    6840
gctactttca tcttgttctc aattctctag ctatgctggc cccttcttgt tctttcccat    6900 tttttttttaa ttttttaaaat ttgtatatat ttatgggtta taagtgaaat ctttttagat    6960
gcataggttg tatagtgata aaatcagggc ttttagggta ttcatcacct gaatgatgta    7020
cattgtaccc cttaagtaat ttctcaccat ccgctgactt cttgcccct gggtattcat    7080 cacctgaatg atgtgcattg taccccttaa gtaatttctc accatccgct gacttcttgc    7140
cccctgggta ttcatcacct gaatgatgtg cattgtaccc cttaagtaat ttctcaccat    7200
ccgctgactt cttgcccct catccttctg aggctccatt gtccatcatt ccacactcta    7260
catctatgtg tacacattat ttagctccta cttataagtg ataacatgca atatttgtct    7320
ttctgtgtct gtcttgtttt acttatgata atggccccca gttctatcta ggctgctgca    7380
aaaggcatga tttcattctt ttttatggct atgttctttc ccaatttaga taaagaacac    7440
tcgcacttgc tcttacttct atttggaata ctaattccta ggcttcttgc attgctttct    7500
ccttctcacc catcaaatct cattttagat accacctctt caaagagggc tttcctgacc    7560
accttggctg aattagccct tcaccatctg attactctct agcacatcac ctgcccattt    7620
tattcatggt acaggtcaaa atctggaatc acctgatttg tttattttct gactccttct    7680
actgagatga aaactctact agagcggaga ttttatctgc ttgtatcagg tactgcttca    7740
aacagcacct gatacagagt aggtggtcaa aagatatttc ttaaacaaat gaacaaataa    7800
aaagtagatc ttttgagagt aaagctcttc cacactacca gagtcattca ggaatgacaa    7860
atcatagaat aacagaattt gatgctttgt gcatatcaga gaaagaaggt ggaaggttgt    7920
caaggtatca tgatgtacca gtcctcgcct cctcaaacac aatctgcaag tcccacagtg    7980
aaaaagtaag ttaactcatg tgaagcgttt tacaaacact tttttaaaag tcttaaaact    8040
cctaagaaag caagatttaa tagtcaaaga agtgagtaaa catgaaatgc ctgaacagag    8100
taatgagcta agcacaaagt tagagacatg ttagttaata tgtcttgaaa gcagcagctc    8160
ctgctttcaa ggagcaagaa caaattgggc aagtgaacac tccttgaata aaatgtgtaa    8220
aattaatttt gggttatgtt ctatactgtg tataatagaa tgataaaaat tatttgacta    8280
gcactttgta gttagaaaat atctctattt acacagttta ccttatttga taagactgtt    8340
gagtgatggg atagcatggt ggacaatcca cataactgag tatcgagaca cctgtatctg    8400
gacccagctc tgttagtaag aagctgtaac ctcagcaagt cactttctct ttctgggtct    8460
ctatttcctt tttggtgaaa tgagagtgtt aggctagatt gcctttgaag tcccatttg    8520
```

```
tctttaaagt cccatctatt gcagtgattt atatttaact catgacaaat caggcttctc    8580
ttattctaag tgcaagacat aaaactttta ttgtggaatt tcaggcatca gtaaatcttt    8640
ttgggtactc acttatgttc ctgaaatcaa tctatttgag tgatcactct tttaggtgcc    8700
caggtaaaca aagaaggcca tggtctttct ttgagtgacc ttctttccct tttaattagt    8760
ctgacctctt taatgtcagt tctgactgat tcatttccct ggtccatctt ccttggtctg    8820
agggccttcc tagtttcata ttgcacttca gttccttcca caccaccatc aaggatggct    8880
gtcaacattc atttgttcta tgttataatt caaggaaaag ttgcccagta gctaatccaa    8940
taaatgccct cttatgggcg gctagagact ttttcctata atttaaatgc atcttctgta    9000
gattatggtc cctccaccac tttacatttg tctgctgtct ccttgctctg ctagtcatgg    9060
aacgtgttgg tagtgggggc agtgtgggat gttcaagggc acgtattggg tagggccaca    9120
tatgggcatt gcttttgtgcc attctttcta tattttggt attttgcatc tcactggaac     9180
ccaactattt ttcatctctt ccacctaaac tatttgatgc ctctgtttct tatatataaa    9240
gtatagctca ctgtagccta tgatcaggaa cctatctgct ttctaaatga aagctgtttt    9300
ggtcagatct agcaattaat tcccttcttc cacttatagc tttcctctgt aactctggtg    9360
taggtatttg gtttatggct ataagatgtg aaacacctga atgattctgt ccatgcaggc    9420
atttcagttc atgatattgt atgtaaaaga tactgattgt ctaggtgttc agaaacacct    9480
atagggctta atattcttac aatcagtttg aaggctggtg atacgcaaag caaactacat    9540 attttctgc ctgctctctc tctttctctc tacatctctc tttctttatc ttttgaaata     9600
tcagtttgga gacttagaat tacataagac ataaacccat ttgatataag aattgctgtg    9660
tatatttgct catctactcc ctcctttggt cctcgagctg ccggtttaga cttttttacag   9720 gacgcaggca tgtgaaggag aaactgtcag tgctaggctg aattctgttg ttaccaagat    9780
ttctagaaaa gtattcctca gtcaggttga ttacagatat agcaaatcta tttttcctag    9840
ggtagtttct gtatgctgcc gggcttataa ctgtctgtca tccagctatt tctctccacc    9900
ttcttgtttg cataacaacc aaggcaactt ccgcaaatca ctgcgtggag acgatgatcc    9960
tgccagctcc cttttggaaa tcgtgaggat cagatcttgg accatgtata atatgatgct   10020
tctaatccaa aagaggaaag gcattgggag tcagctccta gtaagctcc agaattcctg    10080 ctggtacttt tccttccagg aagcaacttc cttgatattt ttttttttaca ggcatatgaa   10140 taaaaactat attttgcagc attgtacact ttttttcctt ttctagaaat tctaaacctc   10200
tgacattggt ggagacattg agtacatttt ttcccatatc cctacttttc agaaggattt   10260
tctctgctcg ttcacttaac attgctgatg cgtcagtctt ttcttcctca tctctttcag   10320
gggctggaga ggcagaggga gacagaggag ctggtactgc agagcggtcg tctgattggc   10380
tggacggtcg tagctgggct ataaaagaga cccctacagg cttagcagga agacgctcag   10440
aggattctga caatatcttt accggagaag aggcaaagta cgctcaaagc cgaagccaca   10500
gctcctcctg ccgcatttct ttcctgcttg cgaattccaa gctgttaaat aagatgtgca   10560
aagggcttgc aggtctgccg gcttcttgct tgaggaggta agattgcttt cagccattaa   10620
ccatattaaa cttttggcta gactttctca gttatttaca tgttgtactt actaacctag   10680
ttctgtgcaa ttagaaacag tgtggtcagg agagcacgac tttctaactt tcctccaaga   10740
ctagctagat attgtgactt aagacatgtg ctccccaaat ttcagccctt atgtgttgtt   10800
ttgtgtgacc tcagttttga gaactgttct attctttaag ccaggtctaa gaaagctagt   10860
tttaattaag aagcgagatg aggtttgagg ctatgtacag tgatctgtaa tatctccatc   10920
```

```
tgtgattact actgctattt gagcatccct ggagtacata aaagcctggc tctgggctttt  10980
ctgattgtat gctacaactt gtttcaggaa aggtacccca gaatgaggtt tggctccatc  11040
atcagaaagg cactatgctt tccgtgtggt ggtgcagtaa ctttcactct ctatgttctt  11100
ataagcaaat gttacaatga gatatgagtt ttaaagccag atcttcctta tctctctgcc  11160
ccatctctag ttcttgaagt gtctcatatg agtttggttg agaaatattg atcattacaa  11220
atcagttaat agttttgtag aagatctcat cttaaagaca ttgttttgtt aatatactcc  11280
cttgattttt taaaagacc ttacagacat acagctattc atttgttttt ggtttgttca  11340
aaaaggtat aaagaaatgc attcagagaa agatcatata ttagccagtt gaaaattaaa  11400
cacaaaatga gtgcatatta cattacttaa tcttgcagtc aaaggtaaaa agtcaaccta  11460
aaggtatact acctgctttc ttatcgcact gcaaatagaa attaccacaa attttatttt  11520
ggaaataatc tcagaaaaca taattttta tgtactatta aaacatttac tttccaaata  11580
ttctgtcatt caggagtatg gaagtatcga tggcttcttt aaaatgaagc aggagggtct  11640
ggcagagagt atctatgaaa taagttcctc tgaccttcac gcttaatttt ctgaatggag  11700
tggagcaaat tacttcaagc ttcacttaac ttgcatatga aatgaaccgt acaaaaatac  11760
aagagtgtca ggagaaagtt atgctctggt aaatattttg caaaacagat aaaagataat  11820
actagagctc tgtcctcaaa gagttaagca gctaatctaa ggaggtaaac tctatgtcag  11880
caggatgaac tgctcttccc tttcctcctc aataaattgc aaatcatcta gtccaacatc  11940
tttaccacca gtgcctgagg ctccagagga gccattgcct tctcaaggtc ataggtgg    12000
tgggtgagtt aggaccaaat ctagaattcc tgactccagt aacttctgaa gtcattttgt  12060
tttttatttt tatggttta ttataagaat acttgctaag cacacttacc ccctgcattg  12120
attaataact ctaggatctc aggtggatcc agcacataga aatatgaatt cgtttctatt  12180
tggacttcat gatatattta cattatcacc ttggaatcac cctaacattc aggattgtat  12240
cttgttataa tcaaaaagga tgttgcatcc cctgaacagt catcagtcag ggaagcagag  12300
gagggaaagt aatcttgcga ggaagagaaa atactattta agggacagtc agagaacata  12360
atggaattca aactttctgg gaaaacctac atacataaat gtattagtgg ccatcctaaa  12420
tgtctttata tcttttgaggc tttatttttcc ctactccaaa tagacacatt tagttattca  12480
tttctttta aatggtattt ctcttttaa actatttctt gactttttta ataaaaagag  12540
atgcaagcaa gaggatattt aataaaaagt aagagagttg agcttaaggc ttattaaaag  12600
acccccttt tctagttagt caggagctct aatgtgccct ggctacctat aaatggtgg   12660
caataaactg gaagctcagt gatgactcta gcctgcttct cctaatagct gttaagcctc  12720
aaatgcccctt tagagtgtgt atgtccttta aagtagctat taagaaggaa agcagcagca  12780
gcagatattg tctagaaaga agcccccaaga agctgaggtt tcagcttggg catttgtttt  12840
cgccatccca tgctccatttt ccctctgctg gaactgtgca cctcagtgta ttctccctct  12900
atacctcaca gcaggaactg cttgcccccc cccccccc ccaacataca tggctggaac  12960
tgaatagact tttactttcc cgaggtgctt ctacagttcc ctctgccagc aggggaacag  13020
atggaaatag caatcacctg ccagaaggtg gcgtgcagca aggatgtgca tcttttgccg  13080
ctactgcttt ctgattccta aaaattactc agagatcact catgtgttca gtgattcagg  13140
ttctgttgaa gataccaaag atattcggtt ggtcaaaatg acgggcatat aaaggcttct  13200
caggtttctg aggtaaactg aagggtcaga attccagttg tggatgaagg aaatggtgtt  13260
```

```
atgactgcct caaggttttg tagcaagtca tagggaacca agaggaatct tgttttcctc    13320
agaggtcatg ccaactccaa ctcccgttcc ctaaactgtc tctgagccat agactagtaa    13380
tggactcttc aagctctacc attaggtatc ttttaaagaa agctggttat tactatttat    13440
tcattttttt ctcttctgtg cagtgcaaaa gatatgaaac atcggctagg tttcctgctg    13500
caaaaatctg attcctgtga acacaattct tcccacaaca agaaggacaa agtggttatt    13560
tgccagaggt aagagaaaag gccttggtga agatgtactt agtattaact atctgatgat    13620
ggggatgttc tgtgagaagg aacttgtgct cctagttaag ccagatttgg atcaagatag    13680
cctccatttt catggagatc ataactacat ttgaaatttc tatacattta gtgaaaaact    13740
gccctcatca ataacatatt ttgtcataac gatggaaaat aaaatctttg ccttcattca    13800
ggatcttaga tttcttgccc caattttttt accatggcat tccaattatt ctgtttctct    13860
ctattttttc tagagtgagc caagaggaag tcaagaaatg ggctgaatca ctggaaaacc    13920
tgattagtca tgaatgtaag tctgacagca acctgggatg aggtactctg ataagacaa    13980 gttatattat gctggtctaa tagaaactgc agcaaggcct ggcttctttc tgatgttcag    14040
actcaggaga ctcttaggt cttaaattca gtctgtttaa aatttaata tgccctagag    14100 ctttgtgata tacaatgaaa agtttatgca ggaaccatgt ggaaaaccat ctctctcatc    14160
acaaggaaaa acggaagaga gaaaaaaaat gataaatatc aataccttct tgcaaaatca    14220
atctcagttt ctcttcccca aattgacctt ggtaattgat agctgcatag gcatttcaga    14280
agcaaaatac ttccttgaaa gaggcttcca acttgagtaa gaatcattag gtagaactgg    14340
gaaccactgg atatcaaaca cagattaggg ttacctgact ccaggtgact tgaaaaaagc    14400
aggggaaaaa gggattgctt gaatccatgc tttatccccc aagtacctca gctttatgtg    14460
aaatagcata tccaagaggc caaccagtgt gatgacaact gtggtccttt ctcctgtatc    14520
ataggtgggc tggcagcttt caaagctttc ttgaagtctg aatatagtga ggagaatatt    14580
gacttctgga tcagctgtga agagtacaag aaaatcaaat caccatctaa actaagtccc    14640
aaggccaaaa agatctataa tgaattcatc tcagtccagg caaccaaaga ggtaggtttt    14700
ttatggatac ataaaaattg tacgtattta tggagtatgt gtgatatttt gatacatgca    14760
tacaatgtga taacaatcaa atcagggcaa ttgctatata catatctcaa acatttatta    14820
tttctacgtg ttgagaacat tccaaatctc ctcttctagc tatcttaaaa tatacaataa    14880
actattgata actatatcac cctaatgtgc tatcaaacac tagaacctat tccctctacc    14940
caactttcta tctattcctt ctacccatta gccaacctga ccaaaaaggt aagcttttat    15000
ggcagagaac tctctggatc ttagtgaagg ttcctagaat agtggagctg actatcataa    15060
tcttgacaac cccaaataaa tcagtttttt aaaaaatctc ttttatccat gtggcttacc    15120
ataacctccc tgcatgaatt tttctgatga atctccccaa tttgttagac agaacagaag    15180
atcttgccct gctctctcta aagcagaaag gttcattctg aacctttcat actctctcac    15240
atgtgccaag gaggaccccca atgtcacttt tgttttttgc ttctgaaata cagagggtgc    15300
actgccactt acaagtcact acaaagcata caggcttgca tcctcaacag ggatataggt    15360
ctaatgaagc cttggccttt gcccctcagg tgaacctgga ttcttgcacc agggaagaga    15420
caagccggaa catgctagag cctacaataa cctgctttga tgaggccag aagaagattt    15480 tcaacctgat ggagaaggat tcctaccgcc gcttcctcaa gtctcgattc tatcttgatt    15540
tggtcaaccc gtccagctgt ggggcagaaa agcagaaagg agccaagagt tcagcagact    15600
gtgcttccct ggtccctcag tgtgcctaat tctcacctga aggcagaggg atgaaatgcc    15660
```

```
aagactctat gctctggaaa acctgaggcc aaatattgat ctgtattaag ctccagtgct   15720
ttatccacat tgtagcctaa tattcatgct gcctgccatg tgtgagtcac ttctacgcat   15780
aaactagata tagcttttgg tgtttgagtg ttcatcaggg tgggacccca ttccagtcca   15840
attttcctaa gtttctttga gggttccatg ggagcaaata tctaaataat ggcctggtag   15900
gtctggattt tcaaagattg ttggcagttt cctcctccca acagttttac ctcgggatgg   15960
ttggttagtg catgtcacat gacatccaca tgcacatgta ttctgttggc cagcacgttc   16020
tccagactct agatgtttag atgaggttga gctatgatat gtgcttgtgt gtatgtctat   16080
gtgtatatat tatatataca ttagacacac atatacatta tttctgtata tagatgtctg   16140
tgtatacata tgtatgtgtg agtgtatgta tacacacaca cacacacaca cacacacact   16200
tttgcaagag tgatgggaaa gaccctaggt gctcataact agagtatgtg tatgtactta   16260
catgggtgtt ttgatctctg ttctttcata ctacatttga acagggcaaa atgaactaac   16320
tgccatgtag gctaagaaag aaatgctaac ctgtggaaag ttggttttgt aaaattccat   16380
ggatcttgct ggagaagcat ccaaggaact tcatgcttga tttgaccact gacagcctcc   16440
accttgagca ctattctaag gagcaaatac cttagctccc ttgagctggt tttctctgat   16500
ggcacttttg agctcctaag ctgccagcct tcccttcttt tcctgggtgc tcagggcatg   16560
cttattagca gctgggttgg tatggagttg gcagacagga tgttcaactt aatgaagaaa   16620
tacagctaag gccttgccag caacacctgc cgtaagttac tggctgagtg agggcataga   16680
agttaaaggt tactgttttt atcctctatc ctttttcct ttcctgatca aggtgctctt    16740 ctcattttt cctgagaacc ttagccatca gatgaggctc cttagtttat tgtggttggt    16800
tgttttttct ttataatggc tctgggctat atgcctatat ttataaacca gcagcagggg   16860
aaagattata ttttataaga gggaacaaat tttcacaatt tgaaagccc acataagttt    16920 tctctttaa ggtagaatct tgttaatttc attccaaaca tcggggctaa cagagactgg    16980
aggcatttct ttttaggctc tgagactaaa tgagaggaaa agaaaagaaa aaaaaaatga   17040
ttgtctaacc aattgtgaga attactgttt gaaacttttc aaggcacatt gaaatacttg   17100
aaaacttctc atttatgtta tttatgatgt tattttgtac gtgttattat tattatattg   17160
ttttataaat ggaggtacag gatatcacct gaattattaa tgaatgccca ggaagtaatt   17220
ttcttctcat tcttctaaaa ctactgcctt tcaaagtgca cacacacgcg tccacataca   17280
ctgcattcgt tgctccagta taaattacat gcatgagcac ctttctggct tttaagccaa   17340
tataatgggc tgcaaaatga agacaccaga gtgtatgcat acaaatctca ctgtattaaa   17400
gatgcaggtt ttctaattgt acccttcttg tctctctggc aatcttgccc ttaatatccc   17460
tggagttcct catcagtgtc attttctgtt atacacagtt ccacaatttt gtctctagtt   17520
gacttcaaat gtgtaacttt attggtcttg ccctattata attgtcatga ctttcagatt   17580
gtatctgaac tcacagactg ctgtcttact aataggtctg gaaggtcacg ctgaatgaga   17640 agtaaaattat tttatgtaat acattttttga gtgtgttttt cagttgtatt tccctgttat   17700
ttcatcacta tttccaatgg tgagcttgcc tgctcatgct ccctggacag aatactcctt   17760
ccttttgcat gcctgtttct atcatgtgct tgataggcct caaagctaat gcttccagtg   17820
aaacacacgc atcttaataa taagggtaaa taaacgctcc atatgaaact atttgcttgg   17880
aaacacatta atgatccaga gacatgctat gagaaacatc agggtgtagg gtgactttag   17940
aaaaatactc atactgagtc tttaatccct cctgtgccag tgaactctgg gaagaaagt    18000
```

```
acaaactgaa tattgtttat tctttagttc atgccactgc tctgcttggc tctactcata   18060
gaaccaaggc aatcttagct tcagagactg caaaacagat taagtgattt gcttgcagat   18120
tctcaatcaa ttttcaaggg atagagttca ccttccagag ccattctttt atttccagtt   18180
acccgcctgt ttgagagatg atagagcagt gggaaattga gagagttgaa aggagctata   18240
gattcttacc caaacttcaa aaatccttcc ctcccttttg ttaattctct ttcctggaaa   18300
agaggtcata aaatgttcac atcctcagta ataggccctg tgctgtgtct attatgtcat   18360
gagactccca tttcctgacc cttctttccc attgtaagag tagtagttac aaggtgttaa   18420
ggatagatga tcttcaacac ttttgagaaa tagatccatt tacggatctg gtaaaaacta   18480
tggaccgaac catcttttaa gaaaaaaatt cagagaggaa tctaaatttt gtgtgctttg   18540
agggaaaact ctcagaatct cccctcaaaa ctatcattct tctcttatac tatagatgtg   18600
tcagactctc actgggactg tatagttgct gctccctgta tttgataata tctatcaaga   18660
actgcagggt aattcaaagt cacgctatta gcagcaagtg tgagcagtgt tggtttcccc   18720
agtctctaca tccctcatcc tttctttctt ctttatggtt gtctattaaa gaaataaaaa   18780
aaaatattgg ctgaccgttt ttctgaagat aatgtatatc aaggaccacc ttttgaaaaa   18840
cactcattat tcgagaacaa agacacaaca tacgagaatc tctgggatac attcaaagca   18900
gtgtgtagag ggaaatttat agcactaaat gcccacaaga gaaagcagga agatctaaa    18960
attgataccc taacatcaca attaaaagaa ctagaaaagc aagagcaaac acattcaaaa   19020
gctagcagaa gacaagaaat aactaagatc agagcagaac tgaaggaaat agagacacaa   19080
aaaaccttca aaaaattaa tgaatccagg agctggtttt ttgaaaagat taacaaaatt    19140
gatagactgc tagcaagact aataaagaag aaaagagaga agaatcaaat agacacaata   19200
aaaaatgata agggggatat caccaccgat cccacagaaa tacaaactac catcagagaa   19260
tactataaac acctctacgc aaataaaacta gaaaatctag aagaaatgga taaattcctc   19320
gatacataca ccctcccaag accaaaccag gaagaagttg aatctctgaa tagaccaata   19380
acaggctctg aaattgaggc aataatcaat agcttaccaa ccaaaaaaag tccaggacca   19440
gatggattca cagctgaatt ctaccagacg tacaaagagg agctggtacc attccttctg   19500
aaactattcc aatcaataga aaagaggga atcctcccta actcattttta tgaggccagc   19560
atcatcctga taccaaagcc tggcagagac acaaccaaaa aagagaattt tagaccaata   19620
tccttgatga acattgatgc aaaaatcctc aataaaatac tggcaaaccg aatccagcag   19680
cacatcaaaa agcttatcca ccatgatcaa gtgggtttca tccctgggat gcaaggctgg   19740
ttcaacatac gcaaatcaat aaatgtaatc cagcatataa acagaaacaa agacaaaaac   19800
cacatgatta tctcaataga tgcagaaaag gcatttgaca aaatttaaca actcttcatg   19860
ctaaaaactc tcaatcaatt aggtattgat gggacgtatc tcaaaataat aagcactatc   19920
tatgacaaac tcacagccaa tatcatactg aatgggcaaa actggaagc attccctttg    19980
aaaacgggca caagacaggg atgccctctc tcaccactcc tattcaacat agtgttggaa   20040
gctctggcca gggcaattag gcaggagaag gaaataaagg gtattcaatt aggagaagag   20100
gaagtcaaat tgtccctgtt tgcagatgac atgattgtat atctagaaaa ccccatcgtc   20160
tcagcccaaa atctccttaa gctgataagc aacttcagca aagtctcagg atacaaaatc   20220
aatgtacaaa aatcacaagc actcttatac atcaataaca gacaaacaga gagccaaatc   20280
atgagtgaac tcccattcac                                              20300
```

<210> SEQ ID NO 4
<211> LENGTH: 480
<212> TYPE: DNA
<213> ORGANISM: Artificial Sequence
<220> FEATURE:
<221> NAME/KEY: misc_feature
<223> OTHER INFORMATION: A genomic sequence occurring upstream of RGS4

<400> SEQUENCE: 4

```
ggattaatca tgacaaaagt aatctaaatc tcgttaagac tacttaatga tcaatctttc      60
cctctgtttt ccctgactat agggaagtga attgccccaa tccttctcta tcacccccct     120
gcagccatgc caatgcctta cctctgttat attcagccat aggggaagct tattctcata     180
gaatcagggg ttggcatgta gtcactagct attcttggtg agactagtga agatgagtga     240
aggaaaatat tgcataggtg aaatctcata ggcacaaata ggtgtttgtg agagtaacaa     300
taaaagaaag tcattcccat actctagtag atgactcatt ttctcctcat tttttttttt     360
tcaaggcgtt ctctacaacg gttaacctag taccaaaaat ccttctcttt tttcttggac     420
aaatcctgtt caagttagca tggcatttac tacgtccaag acattgtcca gatgctgtgg     480
```

<210> SEQ ID NO 5
<211> LENGTH: 420
<212> TYPE: DNA
<213> ORGANISM: Artificial Sequence
<220> FEATURE:
<221> NAME/KEY: misc_feature
<223> OTHER INFORMATION: A genomic sequence occurring upstream of RGS4

<400> SEQUENCE: 5

```
agagaaagaa aggcaggcag caaggagaaa aaacattttt taaaaaaaga aaattaaaat      60
ccatgtaatg tctgatatct gttctgctgt atgtgtagat ctttccatat accaactcat     120
tagccttatt ttacaggtga ggaaaatgag accgagagtc cttcttactt gaccaagttc     180
acacagcaag atcacacatg gtagaaccaa tgttagaacc taggtgtata cttgctcatt     240
caatatgtac aataattgca aaagtttcca taggtcttat tatatatcag gcactataaa     300
tgctatgcat gtgtcaacta atttaaacct aagcaatatt ataaggaagg tactattata     360
gaaatctcag ccttacaggt aagggaacag gaataaagag atgtgaggta atggcccaag     420
```

<210> SEQ ID NO 6
<211> LENGTH: 360
<212> TYPE: DNA
<213> ORGANISM: Artificial Sequence
<220> FEATURE:
<221> NAME/KEY: misc_feature
<223> OTHER INFORMATION: A genomic sequence occurring upstream of RGS4

<400> SEQUENCE: 6

```
ataatctcct ttcaagtttt tatcctgtca cttgctagtt gtgtgatttg ggacaaatca      60
tttaactcct tgtaaaggga gagaaggaag gctgtaaaaa aattaagtaa taaaagata     120 aactccttgt ggtatatttt gttattgttc aaaaatattt attgcccctc ttaggatgtc     180
ttaggtcatt cttgcattgc tataaagaaa tacccaagtc tgggtaattt ataaagaata     240
gaggttaaat tggctcacag ttctgcaggc tgcacaggaa gcatcccact ggcgtctact     300
cacttctggt gaggactcag aaagcttttg cttatgacag caggctaagt gagagcaggt     360
```

<210> SEQ ID NO 7
<211> LENGTH: 420
<212> TYPE: DNA
<213> ORGANISM: Artificial Sequence -continued

```
<220> FEATURE:
<221> NAME/KEY: misc_feature
<223> OTHER INFORMATION: A genomic sequence occurring downstream of
      RGS4

<400> SEQUENCE: 7
catggtattt ttactaccca ttgccttcta ggaaagggta taacaaatag gaaatattaa      60
tatttttaat gcctttgagg gtgttaaaaa gcacaactct aaggactgtt tgtaaattcc     120
aggtcaaatg ttgtttctcc ttctctattt cctaccttgg tgatggcctg atcttatatg     180
gagtcactcc aactagaaac cacagaatca tccctagttc ctacttctga ctcactccat     240
acactcaaaa gtcacctgac tctgcagaat ttctctagaa aaactctatg aaaacctatt     300
cctgcctctc cacctgcata gatgtagctt catccaggct cttatggtgc atggcctcgg     360
ttactgcctt atcctttcta ctggcctctc aatctcccat ctgataccca ttaatgtact     420

<210> SEQ ID NO 8
<211> LENGTH: 360
<212> TYPE: DNA
<213> ORGANISM: Artificial Sequence
<220> FEATURE:
<221> NAME/KEY: misc_feature
<223> OTHER INFORMATION: A genomic sequence occurring downstream of
      RGS4

<400> SEQUENCE: 8
ccaaatactt tttaggcaca ctgggaagtt acattgtttc ttgcaagtga caggttgtcc      60
tttaattagt tctttctctc aaaaagagac tgctgactcc aaactgggaa gaaacccact     120
caccagcaaa atgctgctga attcactctg atagttttct aatctctcat cagtagatga     180
caataatgaa gccagtattg ttaccacaag actcagatat gtctatcacc caagatgatt     240
tctctttaag acgcaataaa agggaactttt tctccccatt tattagcaac taagatgaaa     300
tgagagccag agaaataaag tgaggaagga aagagaattt actaccttta caagctgaaa     360
```